United States Patent
Leimbach et al.

(10) Patent No.: US 10,182,813 B2
(45) Date of Patent: Jan. 22, 2019

(54) SURGICAL STAPLING INSTRUMENT WITH SHAFT RELEASE, POWERED FIRING, AND POWERED ARTICULATION

(71) Applicant: Ethicon Endo-Surgery, LLC, Guaynabo, PR (US)

(72) Inventors: Richard L Leimbach, Cincinnati, OH (US); Tony Siebel, Cincinnati, OH (US); Brett E. Swensgard, West Chester, OH (US); Bryce Hansen, Provo, UT (US); Mark D. Overmyer, Cincinnati, OH (US); Shane Adams, Lebanon, OH (US); Brian Schings, Loveland, OH (US); Sol Posada, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 347 days.

(21) Appl. No.: 14/868,718

(22) Filed: Sep. 29, 2015

(65) Prior Publication Data

US 2017/0086823 A1    Mar. 30, 2017

(51) Int. Cl.
*A61B 17/02*    (2006.01)
*A61B 17/10*    (2006.01)
(Continued)

(52) U.S. Cl.
CPC ...... *A61B 17/068* (2013.01); *A61B 17/07207* (2013.01); *A61B 2017/0046* (2013.01);
(Continued)

(58) Field of Classification Search
CPC .............. A61B 17/068; A61B 17/1155; A61B 2017/00477; A61B 17/105
(Continued)

(56) References Cited

U.S. PATENT DOCUMENTS

| 4,805,823 A | 2/1989 | Rothfuss |
| 5,415,334 A | 5/1995 | Williamson, IV et al. |

(Continued)

FOREIGN PATENT DOCUMENTS

| CA | 2 839 598 A1 | 7/2014 |
| EP | 3 034 015 A2 | 6/2016 |

(Continued)

OTHER PUBLICATIONS

European Search Report, Extended, and Written Opinion dated Apr. 10, 2017 for Application No. EP 16191195.3, 12 pgs.

(Continued)

*Primary Examiner* — Robert Long
(74) *Attorney, Agent, or Firm* — Frost Brown Todd LLC

(57) ABSTRACT

A surgical instrument includes a shaft assembly, a handle assembly, and a latch system configured to operatively couple the shaft and handle assemblies. The latch system includes shaft and a handle lock members respectively connected to the shaft and handle assemblies for inhibiting operative uncoupling of the shaft and handle assemblies. The latch member has a cam surface and a latch member. The latch member is configured to selectively move from a locked position to a released position such that movement of the latch member causes the shaft and handle lock members to disengage and uncouple the shaft and handle assemblies. The latch member is further configured to selectively move from the released position to a removal position such that further movement of the latch member causes the cam surface of the latch member to engage the cam base and urge the shaft assembly in a removal direction.

3 Claims, 21 Drawing Sheets

(51) Int. Cl.
  *A61B 17/072* (2006.01)
  *A61B 17/068* (2006.01)
  *A61B 17/00* (2006.01)
  *A61B 90/00* (2016.01)

(52) U.S. Cl.
  CPC ............ *A61B 2017/00477* (2013.01); *A61B 2090/0807* (2016.02)

(58) Field of Classification Search
  USPC .......................................... 227/175.1–182.1
  See application file for complete search history.

(56) References Cited

U.S. PATENT DOCUMENTS

| | | | |
|---|---|---|---|
| 5,465,895 A | | 11/1995 | Knodel et al. |
| 5,486,185 A | * | 1/1996 | Freitas ............... A61B 17/2909 606/142 |
| 5,507,772 A | * | 4/1996 | Shutt ................. A61B 17/1608 606/205 |
| 5,597,107 A | | 1/1997 | Knodel et al. |
| 5,632,432 A | | 5/1997 | Schultze et al. |
| 5,673,840 A | | 10/1997 | Schultze et al. |
| 5,704,534 A | | 1/1998 | Huitema et al. |
| 5,814,055 A | | 9/1998 | Knodel et al. |
| 6,783,524 B2 | | 8/2004 | Anderson et al. |
| 6,978,921 B2 | | 12/2005 | Shelton, IV et al. |
| 7,000,818 B2 | | 2/2006 | Shelton, IV et al. |
| 7,143,923 B2 | | 12/2006 | Shelton, IV et al. |
| 7,303,108 B2 | | 12/2007 | Shelton, IV |
| 7,367,485 B2 | | 5/2008 | Shelton, IV et al. |
| 7,380,695 B2 | | 6/2008 | Doll et al. |
| 7,380,696 B2 | | 6/2008 | Shelton, IV et al. |
| 7,404,508 B2 | | 7/2008 | Smith et al. |
| 7,434,715 B2 | | 10/2008 | Shelton, IV et al. |
| 7,721,930 B2 | | 5/2010 | McKenna et al. |
| 8,154,239 B2 | | 4/2012 | Katsuki et al. |
| 8,408,439 B2 | | 4/2013 | Huang et al. |
| 8,453,914 B2 | | 6/2013 | Laurent et al. |
| 9,072,535 B2 | | 7/2015 | Shelton, IV et al. |
| 9,186,142 B2 | | 11/2015 | Fanelli et al. |
| 9,517,065 B2 | | 12/2016 | Simms et al. |
| 9,826,976 B2 | * | 11/2017 | Parihar ................ A61B 17/068 |
| 2012/0104071 A1 | * | 5/2012 | Bryant ............ A61B 17/07207 227/175.1 |
| 2013/0106095 A1 | * | 5/2013 | Chen ...................... F16L 37/18 285/85 |
| 2013/0200131 A1 | * | 8/2013 | Racenet ............... A61B 17/072 227/180.1 |
| 2013/0324978 A1 | * | 12/2013 | Nicholas ............. A61B 17/068 606/1 |
| 2014/0207182 A1 | * | 7/2014 | Zergiebel ........... A61B 17/2841 606/205 |
| 2014/0239036 A1 | | 8/2014 | Zerkle et al. |
| 2014/0239037 A1 | | 8/2014 | Boudreaux et al. |
| 2014/0239038 A1 | | 8/2014 | Leimbach et al. |
| 2014/0239040 A1 | | 8/2014 | Fanelli et al. |
| 2014/0239041 A1 | | 8/2014 | Zerkle et al. |
| 2014/0239043 A1 | | 8/2014 | Simms et al. |
| 2014/0239044 A1 | | 8/2014 | Hoffman |
| 2014/0263541 A1 | | 9/2014 | Leimbach et al. |
| 2014/0305989 A1 | * | 10/2014 | Parihar ............. A61B 17/0686 227/176.1 |
| 2014/0305992 A1 | * | 10/2014 | Kimsey ............... A61B 17/068 227/176.1 |
| 2014/0373652 A1 | * | 12/2014 | Zergiebel ................ F16H 19/02 74/89.23 |
| 2015/0272575 A1 | | 10/2015 | Leimbach et al. |
| 2016/0157856 A1 | * | 6/2016 | Williams ............. A61B 17/068 227/175.1 |
| 2016/0192934 A1 | * | 7/2016 | Williams ............. A61B 17/105 227/175.1 |
| 2016/0192938 A1 | * | 7/2016 | Sgroi, Jr. ........... A61B 17/1155 227/175.1 |
| 2017/0079660 A1 | * | 3/2017 | Sgroi ................... A61B 17/068 |

FOREIGN PATENT DOCUMENTS

| | | |
|---|---|---|
| WO | WO 2007/038538 A1 | 4/2007 |
| WO | WO 2008/073362 A2 | 6/2008 |

OTHER PUBLICATIONS

International Search Report and Written Opinion dated Mar. 13, 2017 for Application No. PCT/US2016/052772, 16 pgs.

* cited by examiner

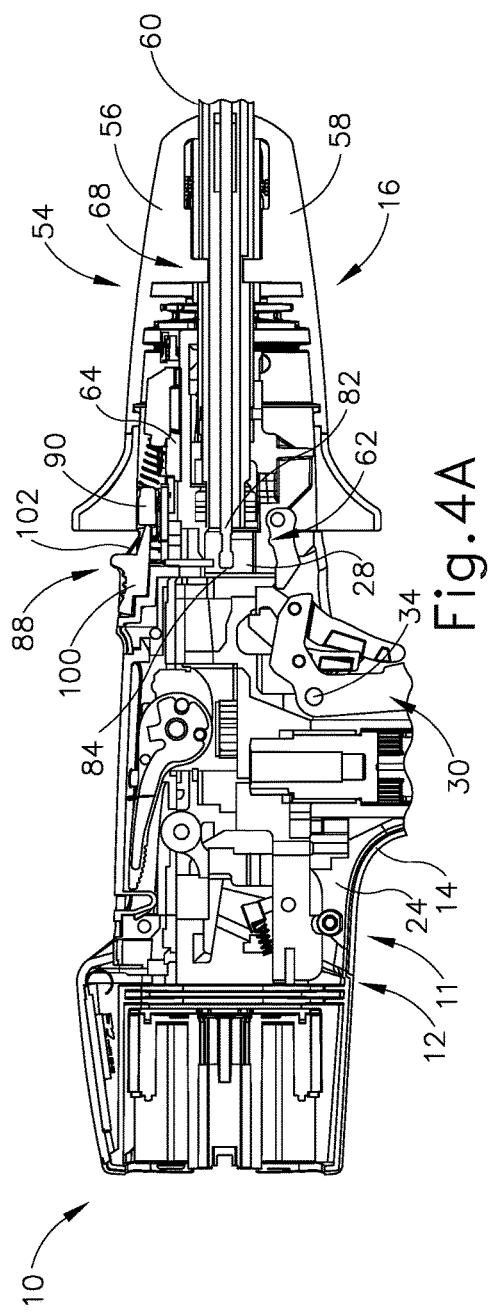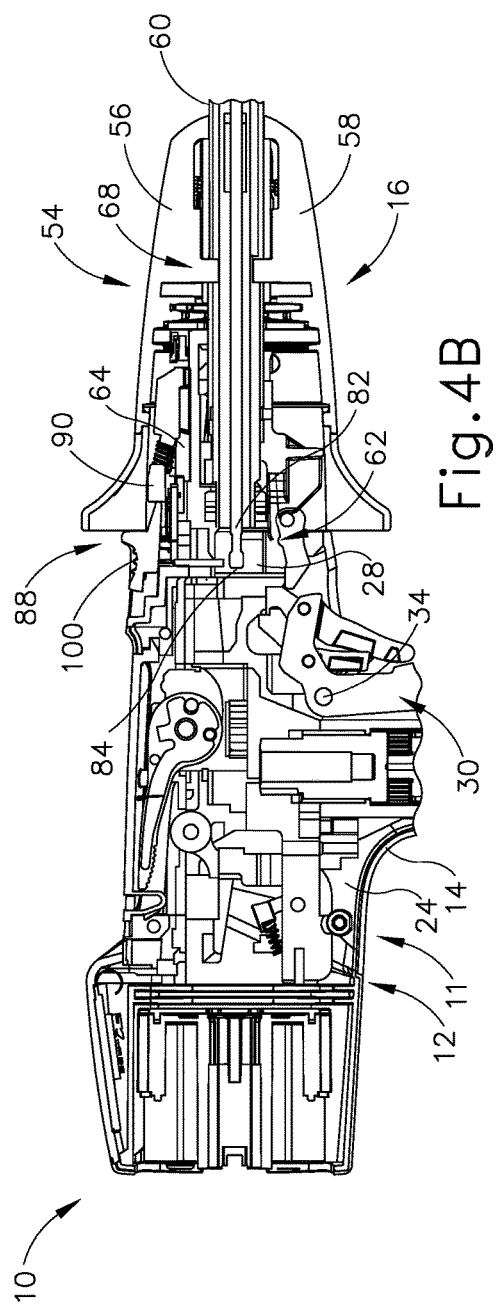

SURGICAL STAPLING INSTRUMENT WITH SHAFT RELEASE, POWERED FIRING, AND POWERED ARTICULATION

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014, now U.S. Pat. No. 9,186,142, issued Nov. 17, 2015; U.S. Patent Application Publication No. 2014/0239041, entitled "Lockout Feature for Movable Cutting Member of Surgical Instrument," Published Aug. 28, 2014, now U.S. Pat. No. 9,717,497, issued Aug. 1, 2017; U.S. Patent Application Publication No. 2014/0239042, entitled "Integrated Tissue Positioning and Jaw Alignment Features for Surgical Stapler," published Aug. 28, 2014, now U.S. Pat. No. 9,517,065, issued Dec. 13, 2016; U.S. Patent Application Publication No. 2014/0239036, entitled "Jaw Closure Feature for End Effector of Surgical Instrument," Published Aug. 28, 2014, now U.S. Pat. No. 9,839,421, issued Dec. 12, 2017; U.S. Patent Application Publication No. 2014/0239040, entitled "Surgical Instrument with Articulation Lock having a Detenting Binary Spring," published Aug. 24, 2014, now U.S. Pat. No. 9,867,615, issued Jan. 16, 2018; U.S. Patent Application Publication No. 2014/0239043, entitled "Distal Tip Features for End Effector of Surgical Instrument," published Aug. 28, 2014, now U.S. Pat. No. 9,622,746, issued Apr. 18, 2017; U.S. Patent Application Publication No. 2014/0239037, entitled "Staple Forming Features for Surgical Stapling Instrument," filed Aug. 28, 2014, now U.S. Pat. No. 10,092,292, issued Oct. 9, 2018; U.S. Patent Application Publication No. 2014/0239038, entitled "Surgical Instrument with Multi-Diameter Shaft," published Aug. 28, 2014, now U.S. Pat. No. 9,795,379, issued Oct. 24, 2017; and U.S. Patent Application Publication No. 2014/0239044, entitled "Installation Features for Surgical Instrument End Effector Cartridge," published Aug. 28, 2014, now U.S. Pat. No. 9,808,248, issued Nov. 7, 2017. The disclosure of each of the above-cited U.S. patent applications is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4A depicts a cross-sectional side view of the instrument of FIG. 1, taken along line 4-4 of FIG. 1, with the shaft assembly operatively coupled to the handle assembly;

FIG. 4B depicts a cross-sectional side view of the instrument of FIG. 1, taken along line 4-4 of FIG. 1, with the shaft assembly at an initial stage of operatively decoupling from the handle assembly;

Figure 1:
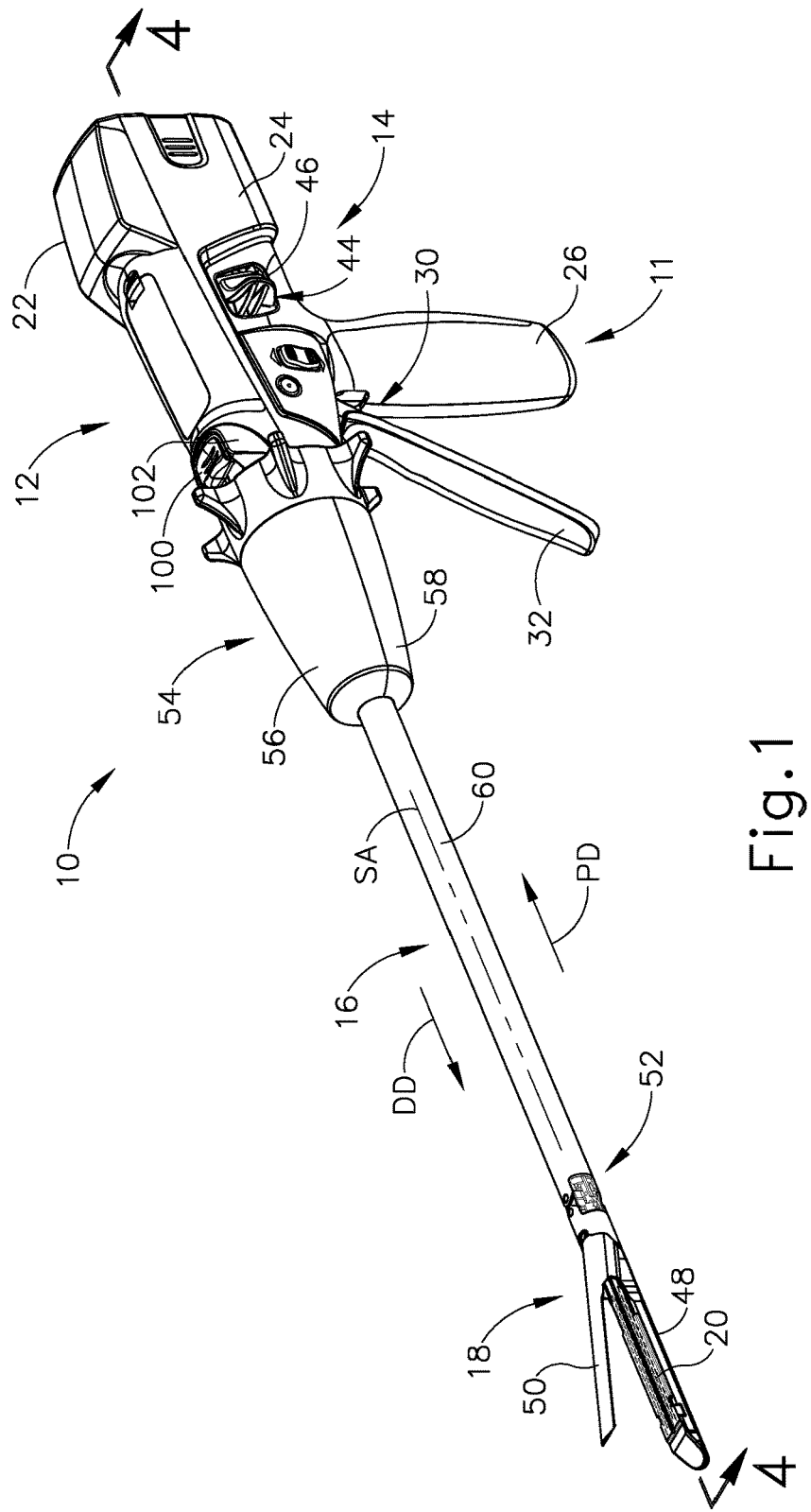
FIG. 1 depicts a perspective view of an exemplary surgical instrument including an interchangeable shaft assembly and a handle assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator. Although the surgical instruments described herein comprise motorized implements for cutting and stapling, it will be appreciated that the battery configurations described herein may be used with any suitable type of electrical surgical instrument such as cutters, claspers, staplers, RF cutter/coagulators, ultrasonic cutter/coagulators, and laser cutter/coagulators, for example.

I. Overview of Exemplary Surgical Instrument

FIG. 1 depicts a motor-driven surgical cutting and fastening instrument (10) that may or may not be reused. In the illustrated embodiment, surgical instrument (10) includes a handle assembly (11) having a housing (12). At least a portion of the housing (12) forms a handle (14) configured to be grasped, manipulated and actuated by the clinician. Housing (12) is configured for operative attachment to an interchangeable shaft assembly (16) that has a surgical end effector (18) operatively coupled thereto that is configured to perform one or more surgical tasks or procedures. It will be appreciated that the various unique and novel arrangements of the various forms of interchangeable shaft assemblies disclosed herein may also be effectively employed in connection with robotically-controlled surgical systems. Thus, the term "housing" may also encompass a housing or similar portion of a robotic system that houses or otherwise operatively supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operatively control a surgical instrument. For example, the interchangeable shaft assemblies disclosed herein may be employed with various robotic systems, instruments, components and methods disclosed in U.S. Pat. No. 9,072,535, entitled "Surgical Stapling Instruments with Rotatable Staple Deployment Arrangements," issued Jul. 7, 2015, the disclosure of which is incorporated by reference herein.

Handle assembly (11) is shown in connection with the interchangeable shaft assembly (16) that includes end effector (18) that comprises surgical cutting and fastening device (10) operatively support a surgical staple cartridge (20) therein. Housing (12) may be configured for use in connection with interchangeable shaft assemblies that include end effectors that are adapted to support different sizes and types of staple cartridges, have different shaft lengths, sizes, and types, etc. In addition, handle assembly (11) may also be effectively employed with a variety of other interchangeable shaft assemblies including those assemblies that are configured to apply other motions and fauns of energy such as, for example, radio frequency (RF) energy, ultrasonic energy and/or motion to end effector arrangements adapted for use in connection with various surgical applications and procedures. Furthermore, end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. Various examples of such cartridges are disclosed in various references that are cited herein.

Figure 2:
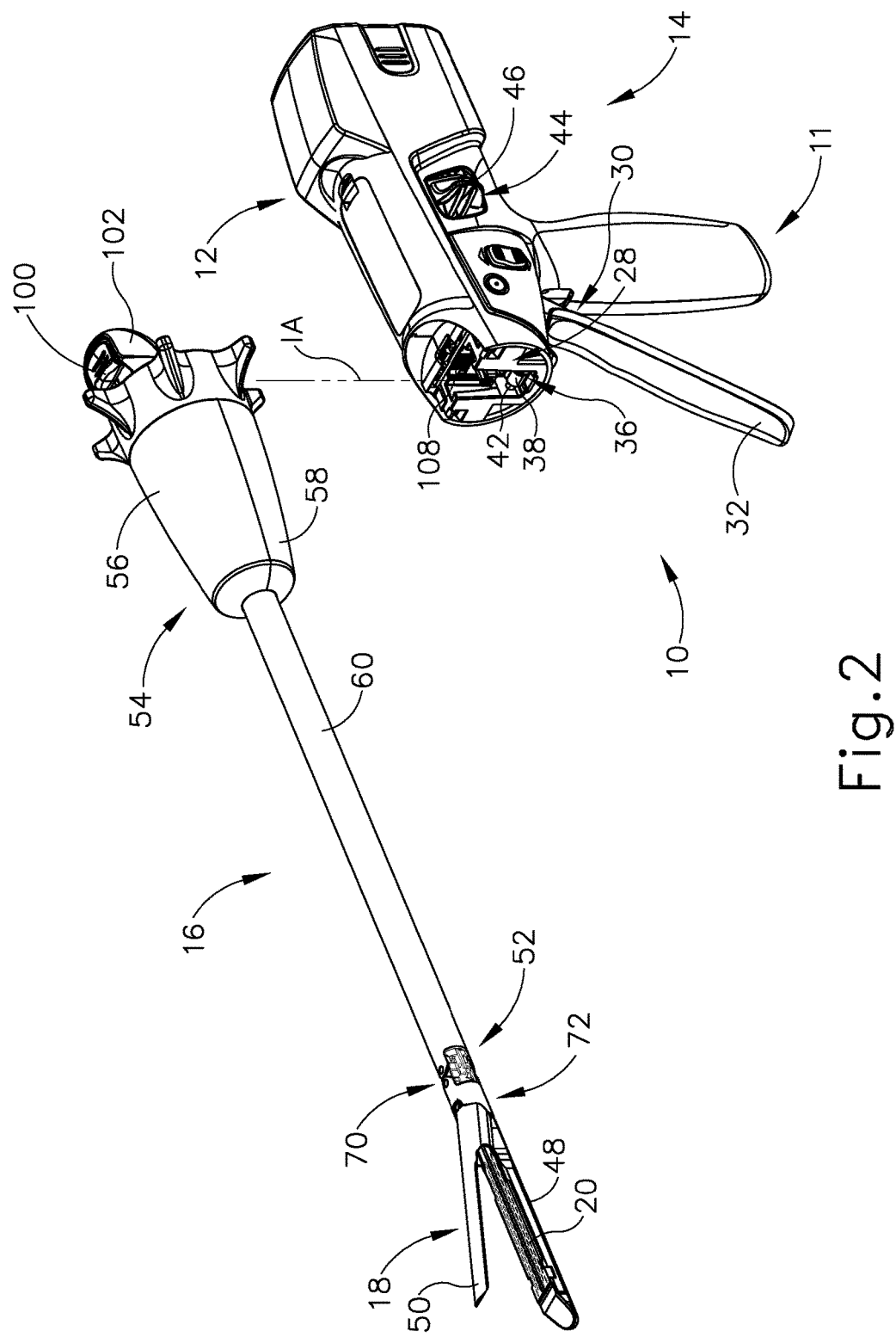
FIG. 2 depicts an perspective view of the instrument of FIG. 1, showing the shaft assembly disassembled from the handle assembly of the instrument.
Figure 3:
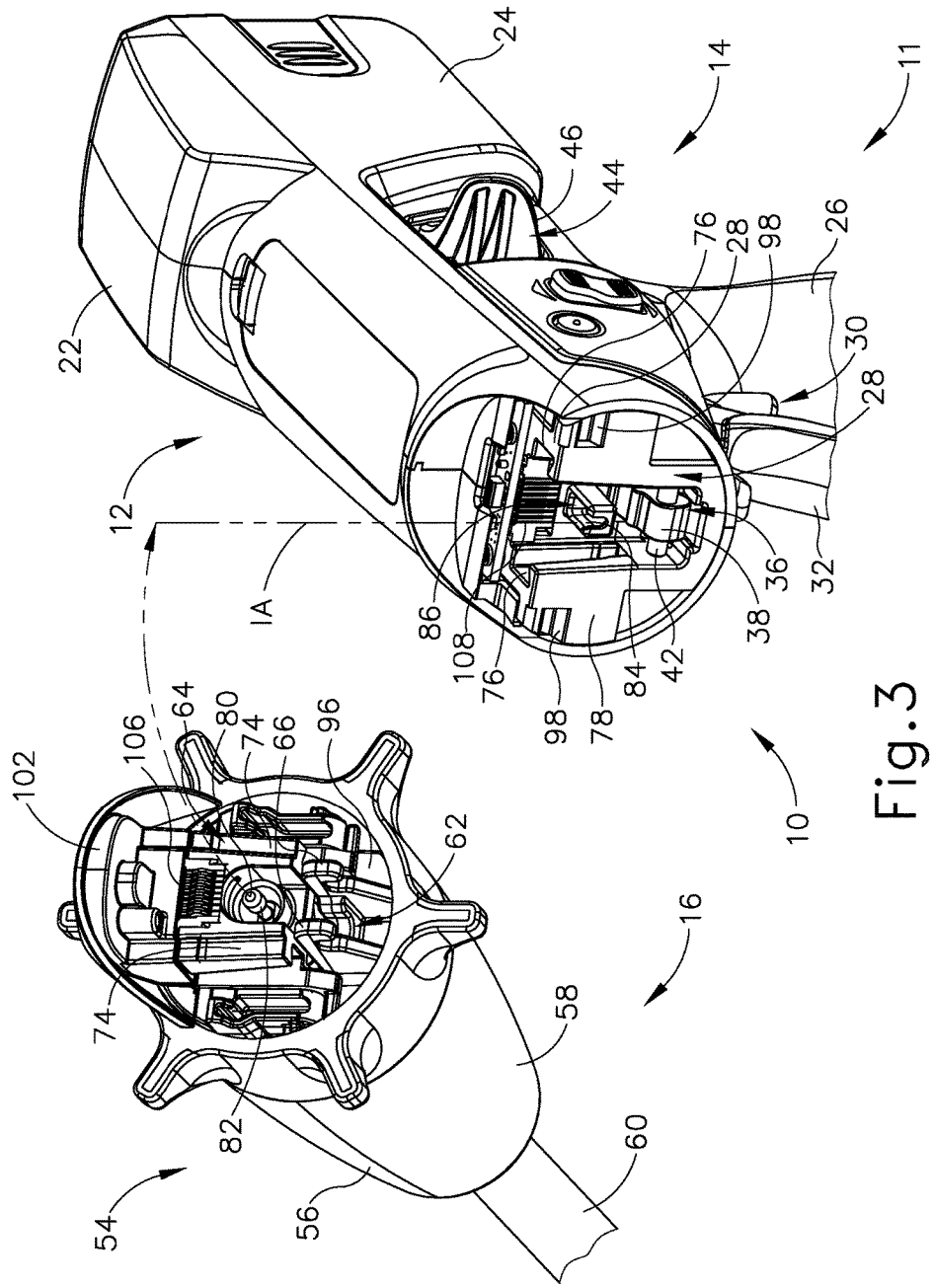
FIG. 3 depicts a partial perspective view of the instrument of FIG. 1, showing the shaft assembly disassembled from the handle assembly of the instrument.

FIG. 1 illustrates surgical instrument (10) with interchangeable shaft assembly (16) operatively coupled to handle assembly (11). FIGS. 2-3 illustrate attachment of interchangeable shaft assembly (16) to housing (12) of handle (14). Handle (14) includes a pair of interconnectable handle housing segments (22, 24) that may be interconnected by screws, snap features, adhesive, etc. In the illustrated arrangement, handle housing segments (22, 24) cooperate to form a pistol grip portion (26) that can be gripped and manipulated by the clinician. As will be discussed in further detail below, handle (14) operatively supports a plurality of drive systems therein that are configured to generate and apply various control motions to corresponding portions of interchangeable shaft assembly (16) that is operatively attached thereto.

Handle (14) further includes a frame (28) that operatively supports a plurality of drive systems. For example, frame (28) can operatively support a "first" or closure drive system, generally designated as (30), which may be employed to apply closing and opening motions to interchangeable shaft assembly (16) that is operatively attached or coupled thereto. In one example, closure drive system (30) includes an actuator in the form of a closure trigger (32) that is pivotally supported by frame (28). More specifically, closure trigger (32) is pivotally coupled to housing (14) by a pin (34) (see FIG. 4A). Such arrangement enables closure trigger (32) to be manipulated by a clinician such that when the clinician grips pistol grip portion (26) of handle (14), closure trigger (32) may be easily pivoted from a starting or "unactuated" position toward pistol grip portion (26) to an "actuated" position and more particularly to a fully compressed or fully actuated position. Closure trigger (32) may be biased into the unactuated position by spring or other biasing arrangement (not shown). In various examples, closure drive system (30) further includes a closure linkage assembly (36) pivotally coupled to closure trigger (32). The closure linkage assembly (36) may include a first closure link (not shown) and a second closure link (38) that are pivotally coupled to closure trigger (32) by a pin (not shown). Second closure link (38) may also be referred to herein as an "attachment member" and include a transverse attachment pin (37).

Still referring to FIGS. 1-3, first closure link (not shown) is configured to cooperate with a closure release assembly (44) that is pivotally coupled to frame (28). In at least one example, closure release assembly (44) has a release button assembly (46) with a distally protruding locking pawl (not shown) formed thereon. Release button assembly (46) may be pivoted in a counterclockwise direction by a release spring (not shown). As the clinician depresses closure trigger (32) from its unactuated position toward pistol grip portion (26) of handle (14), first closure link (not shown) pivots upward to a point where a locking pawl (not shown) drops into retaining engagement with first closure link (not shown) thereby preventing closure trigger (32) from returning to the unactuated position. Thus, closure release assembly (44) serves to lock closure trigger (32) in the fully actuated position. When the clinician desires to unlock closure trigger (32) from the actuated position to return to the unactuated position, the clinician simply pivots closure release button assembly (46) such that locking pawl (not shown) is moved out of engagement with the first closure link (not shown). When the locking pawl (not shown) has been moved out of engagement with first closure link (not shown), closure trigger (32) may pivot back to the unactuated position. Other closure trigger locking and release arrangements may also be employed.

Interchangeable shaft assembly (16) includes surgical end effector (18) that comprises an elongated channel (48) configured to operatively support staple cartridge (20) therein. End effector (18) of the present example further includes an anvil (50) that is pivotally supported relative to elongated channel (48). Interchangeable shaft assembly (16) further includes an articulation joint (52) and an articulation lock (not shown) that can be configured to releasably hold end effector (18) in a desired position relative to a longitudinal axis of shaft assembly (16). By way of example only, end effector (18), articulation joint (52), and articulation lock (not shown) may be configured and operable in accordance with at least some of the teachings of U.S. Pub. No. 2014/0263541, entitled "Articulatable Surgical Instrument Comprising an Articulation Lock," published Sep. 18, 2014, now abandoned. Alternatively, end effector (18), articulation joint (52), and articulation lock (not shown) may be configured and operable in accordance with at least some of the teachings of any other reference(s) cited herein; or may be configured and operable in any other suitable fashion.

Interchangeable shaft assembly (16) further includes a proximal housing or nozzle (54) comprised of nozzle portions (56, 58). Interchangeable shaft assembly (16) further includes a closure tube (60) which can be utilized to close and/or open anvil (50) of end effector (18). Shaft assembly (16) also includes a closure shuttle (62) that is slidably supported within a chassis (64) such that it may be axially moved relative thereto. Closure shuttle (62) includes a pair of proximally-protruding hooks (66) that are configured for attachment to attachment pin (42) that is attached to second closure link (38). A proximal end (68) (see FIG. 5A) of closure tube (60) is coupled to closure shuttle (62) for relative rotation thereto. A closure spring (not shown) is journaled on closure tube (60) and serves to bias closure tube (60) in the proximal direction (PD), which can serve to pivot closure trigger (32) into the unactuated position when shaft assembly (16) is operatively coupled to handle (14). Additional details regarding one or more features of alternative shaft assemblies will be provided below in greater detail.

In the present example, articulation joint (52) includes a double pivot closure sleeve assembly (70). The double pivot closure sleeve assembly (70) includes an end effector closure sleeve assembly (72) for engaging an opening tab on anvil (50) in the various manners described in U.S. Pub. No. 2014/0263541, now abandoned, the disclosure of which is incorporated by reference herein. While shaft assembly (16) of the present example includes articulation joint (52), other interchangeable shaft assemblies may lack articulation capabilities.

Referring to FIGS. 3-4B, chassis (64) includes a pair of tapered attachment portions (74) formed thereon that are adapted to be received within corresponding dovetail slots (76) formed within a distal attachment flange portion (78) of frame (28). Each dovetail slot (76) may be tapered or generally V-shaped to seatingly receive attachment portions (74) therein. A shaft attachment lug (80) is formed on the proximal end of an intermediate firing shaft (82). As such, when interchangeable shaft assembly (16) is coupled to handle (14), shaft attachment lug (80) is received in a firing shaft attachment cradle (84) formed in a distal end of a longitudinal drive member (86).

One example of shaft assembly (16) includes a latch system (88) for removably coupling shaft assembly (16) to handle assembly (11) and, more specifically, to frame (28). As can be seen in FIGS. 4A-5B, for example, latch system (88) includes a lock member or lock yoke (90) that is movably coupled to chassis (64). In the illustrated example, lock yoke (90) has a U-shape with two spaced downwardly extending legs (92). Legs (92) each have a pivot lug (94) formed thereon that are adapted to be received in corresponding holes (not shown) formed in chassis (64). Such arrangement facilitates pivotal attachment of lock yoke (90) to chassis (64). Lock yoke (90) includes two proximally protruding lock lugs (96) that are configured for releasable engagement with corresponding lock detents or grooves (98) in distal attachment flange portion (78) of frame (28) (See FIG. 3). In various forms, lock yoke (90) is biased in the proximal direction by spring (91) or other biasing member (e.g., as seen in FIGS. 7A-7C, 10A-10C, and 12A-12B, which are described in greater detail below). Actuation of lock yoke (90) may be accomplished by a latch button (100) that is slidably mounted on a latch actuator assembly (102) that is mounted to chassis (64). Latch button (100) may be biased in a proximal direction relative to lock yoke (90). As will be discussed in further detail below, lock yoke (90) may be moved to an unlocked position by urging latch button (100) the in distal direction, which also causes lock yoke (90) to pivot out of retaining engagement with distal attachment flange portion (78) of frame (28). When lock yoke (90) is in "retaining engagement" with distal attachment flange portion (78) of frame (28), lock lugs (96) are retainingly seated within the corresponding lock detents or grooves (98) in distal attachment flange portion (78).

When employing an interchangeable shaft assembly that includes an end effector of the type described herein that is adapted to cut and fasten tissue, as well as other types of end effectors, it may be desirable to prevent inadvertent detachment of the interchangeable shaft assembly (16) from the handle assembly (11) during actuation of end effector (18). For example, in use, the clinician may actuate the closure trigger (32) to grasp and manipulate the target tissue into a desired position. Once the target tissue is positioned within end effector (18) in a desired orientation, the clinician may then fully actuate closure trigger (32) to close anvil (50) and clamp the target tissue in position for cutting and stapling. In that instance, closure drive system (30) has been fully actuated. After the target tissue has been clamped in the end effector (18), it may be desirable to prevent the inadvertent detachment of shaft assembly (16) from handle assembly (11).

Figure 5A:
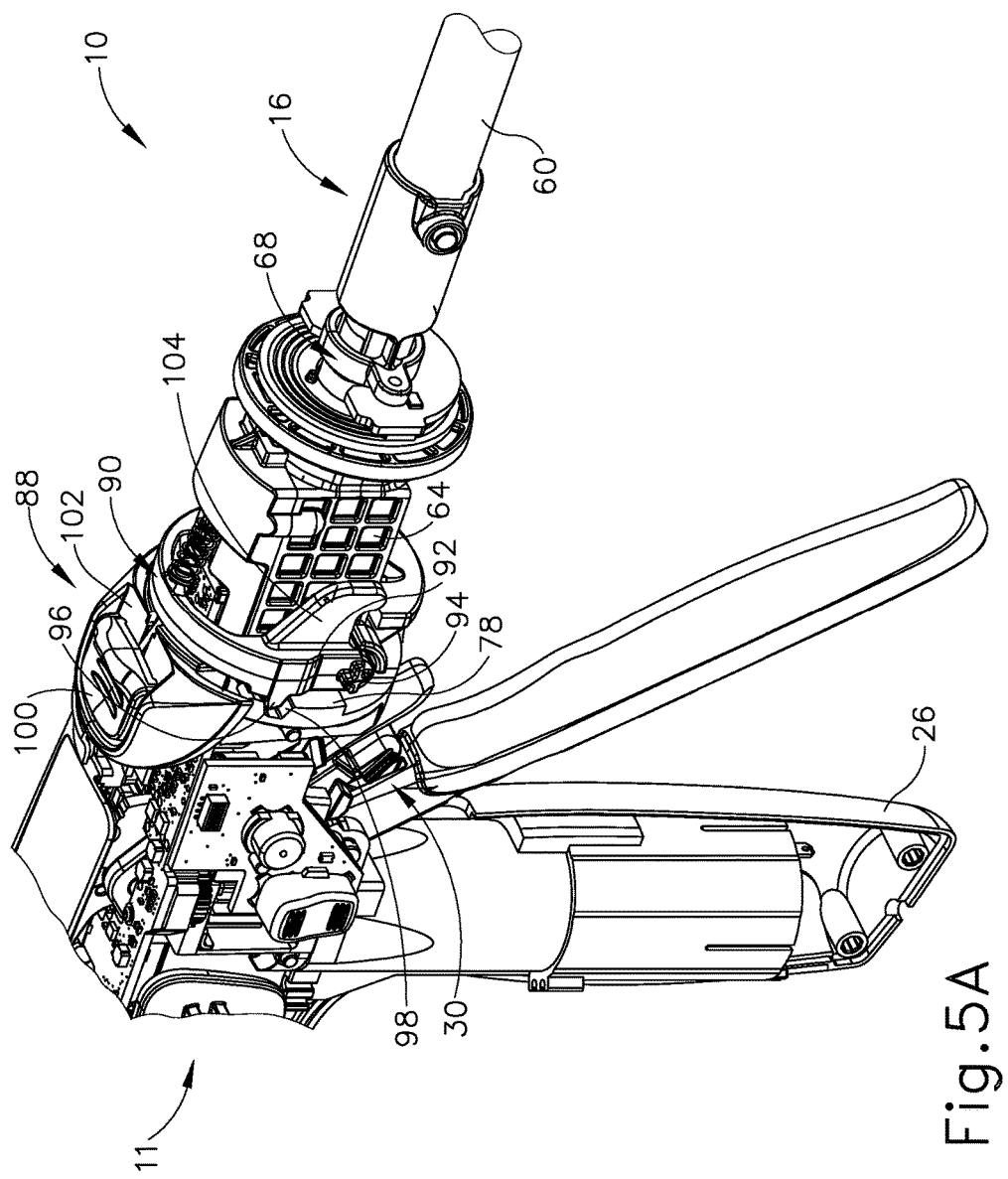
FIG. 5A depicts a perspective view of the instrument of FIG. 1, with a portion of housing removed to show the shaft assembly operatively coupled to the handle assembly.
Figure 5B:
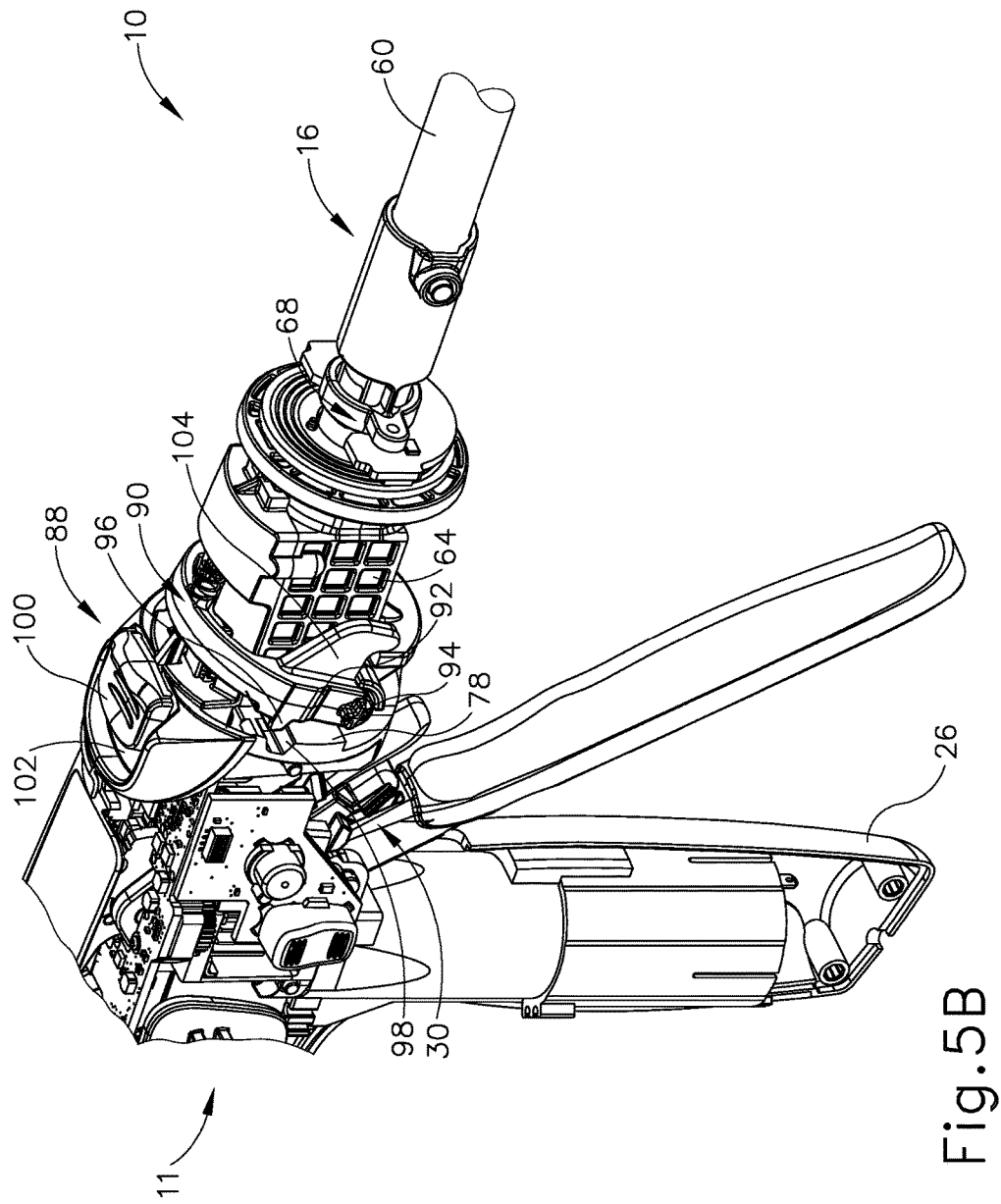
FIG. 5B depicts a perspective view of the instrument of FIG. 1, with a portion of housing removed to show the shaft assembly at an initial stage of operatively decoupling from the handle assembly.

To this end, FIGS. 5A-5B show lock yoke (90) including a pair of lock hooks (104) that are adapted to contact corresponding lock lugs (96) that are formed on closure shuttle (62). Referring to FIGS. 3 and 5A-5B, when closure shuttle (62) is in an unactuated position (i.e., the first drive system (30) is unactuated and anvil (50) is open), lock yoke (90) may be pivoted in a distal direction to unlock interchangeable shaft assembly (16) from handle assembly (11). When in that position, lock hooks (104) do not contact the lock lugs (96) on closure shuttle (62). However, when closure shuttle (62) is moved to an actuated position (i.e., the first drive system (30) is actuated and the anvil (50) is in the closed position), lock yoke (90) is prevented from being pivoted to an unlocked position. Stated another way, if the clinician were to attempt to pivot lock yoke (90) to an unlocked position or, for example, lock yoke (90) were inadvertently bumped or contacted in a manner that might otherwise cause it to pivot distally, lock hooks (104) on lock yoke (90) will contact lock lugs (96) on closure shuttle (62) and prevent movement of lock yoke (90) to an unlocked position.

Attachment of interchangeable shaft assembly (16) to handle (14) will now be described with reference to FIGS. 3-5B. To commence the coupling process, the clinician may position chassis (64) of interchangeable shaft assembly (16) above or adjacent to distal attachment flange portion (78) of frame (28) such that tapered attachment portions (74) formed on chassis (64) are aligned with dovetail slots (76) in frame (28). The clinician may then move shaft assembly (16) along an installation axis (IA) that is perpendicular to the longitudinal axis of shaft assembly (16) to seat attachment portions (74) in "operative engagement" with the corresponding dovetail receiving slots (76). In doing so, shaft attachment lug (80) on intermediate firing shaft (82) will also be seated in cradle (84) in the longitudinally movable drive member (86) and the portions of pin (42) on second closure link (38) will be seated in the corresponding hooks (66) in closure shuttle (62). As used herein, the term "operative engagement" in the context of two components means that the two components are sufficiently engaged with each other so that upon application of an actuation motion thereto, the components may carry out their intended action, function, and/or procedure.

As discussed above, at least five systems of the interchangeable shaft assembly (16) may be operatively coupled with at least five corresponding systems of the handle (14). A first system comprises a frame system that couples and/or aligns the frame or spine of shaft assembly (16) with frame (28) of the handle (14). A second system is closure drive system (30) that may operatively connect closure trigger (32) of handle (14) and closure tube (60) and anvil (50) of shaft assembly (16). As outlined above, closure shuttle (62) of shaft assembly (16) engages with pin (42) on second closure link (38). A third system is a firing drive system operatively connecting a firing trigger the handle (14) with the intermediate firing shaft (82) of the shaft assembly (16). As outlined above, the shaft attachment lug (80) operatively connects with the cradle (84) of the longitudinal drive member (86). A fourth system is an electrical system that can signal to a controller in the handle (14), such as microcontroller, that the shaft assembly (16) has been operatively engaged with the handle (14) to conduct power and/or communicate signals between the shaft assembly (16) and the handle (14). For instance, the shaft assembly (16) includes an electrical connector (106) that is operatively mounted to a shaft circuit board (not shown). Electrical connector (106) is configured for mating engagement with a corresponding electrical connector (108) on a handle control board (not shown). Further details regarding the circuitry and control systems may be found in U.S. Pub. No. 2014/0263541, now abandoned, the disclosure of which is incorporated by reference herein. The fifth system is latch system (88) for releasably locking the shaft assembly (16) to the handle (14).

The various shaft assemblies (16) disclosed herein may employ sensors and various other components that require electrical communication with the controller in the housing (12). These shaft assemblies (16) generally are configured to be able to rotate relative to the housing necessitating a connection that facilitates such electrical communication between two or more components that may rotate relative to each other. When employing end effectors of the types disclosed herein, the connector arrangements must be relatively robust in nature while also being somewhat compact to fit into the shaft assembly connector portion. In addition to the foregoing, instrument (10) may be constructed and operable in accordance with at least some of the teachings of U.S. patent application Ser. No. 14/226,142, entitled "Surgical Instrument Comprising a Sensor System," filed Mar. 26, 2014, now U.S. Pat. No. 9,913,642, issued Mar. 3, 2018, the disclosure of which is incorporated by reference herein. In addition or in the alternative, instrument (10) may be constructed and operable in accordance with at least some of the teachings of any of the various other references that are cited herein.

II. Surgical Instrument with an Ejection Latch System

While the above surgical instrument (10) provides for interchangeable shaft assembly (16), it will be appreciated that shaft assembly (16) is coupled and uncoupled by movement along installation axis (IA). As such, the operator may fail to remember the direction of removing the shaft assembly (16) from handle assembly (11) and inadvertently attempt to remove shaft assembly (16) in another, incorrect direction (e.g., by pulling shaft assembly (16) along the longitudinal axis of shaft assembly (16)). At best, this attempted removal may result in wasted time and frustration during surgery, particularly during complex and time sensitive surgical procedures. At worst, the operator may inadvertently damage surgical instrument (10) during or upon the improper removal. It may therefore be desirable to provide a surgical instrument (210) having an ejection latch system (288) that is configured to at least partially remove shaft assembly (16) from handle assembly (11) in order to more readily indicate to the operator the direction of removing shaft assembly (16). It will be understood that the features discussed below may be readily incorporated into surgical instrument (10) discussed above. To this end, like numbers indicate like features described above in greater detail.

Figure 6:
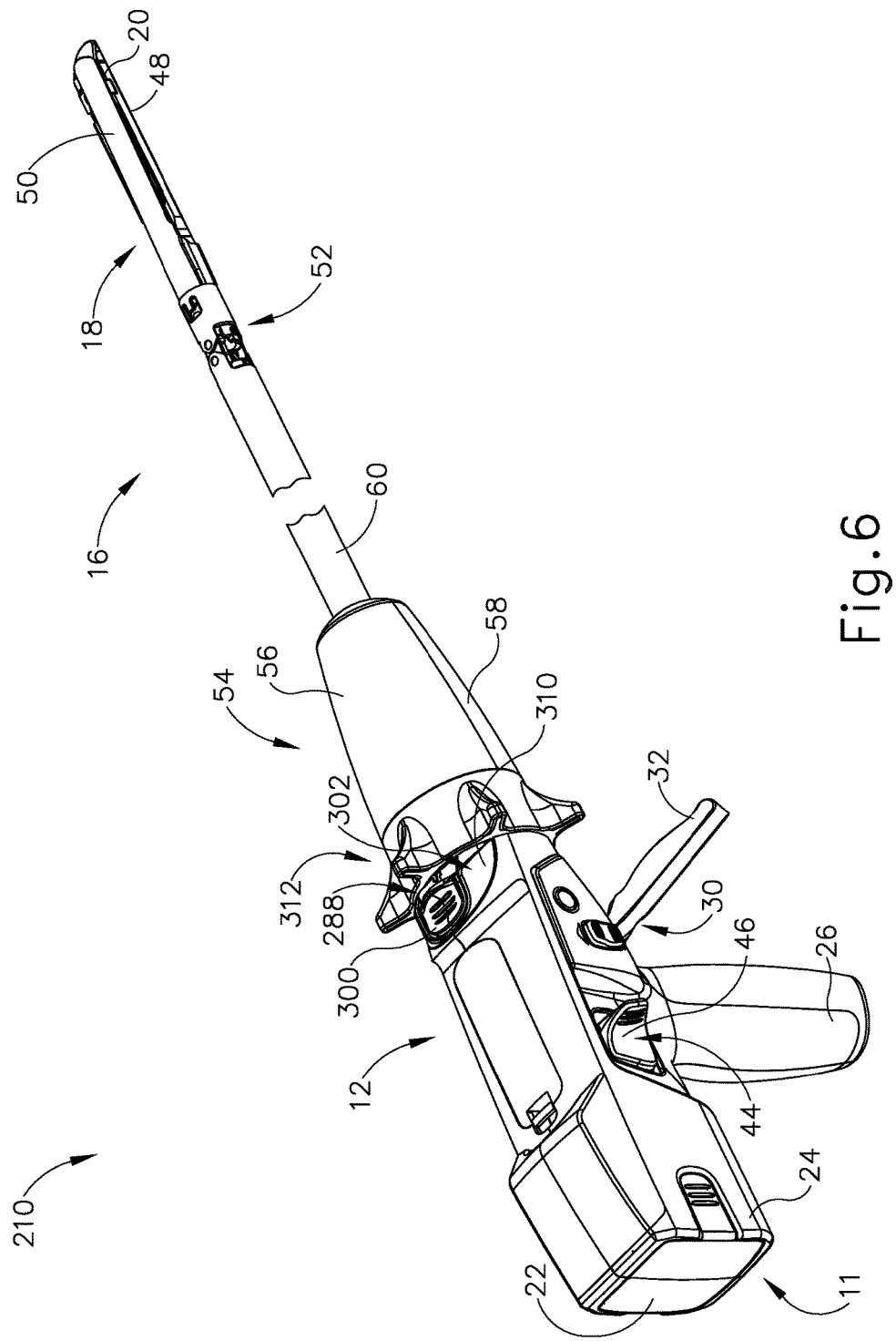
FIG. 6 depicts a perspective view of another exemplary surgical stapling instrument.
Figure 7A:
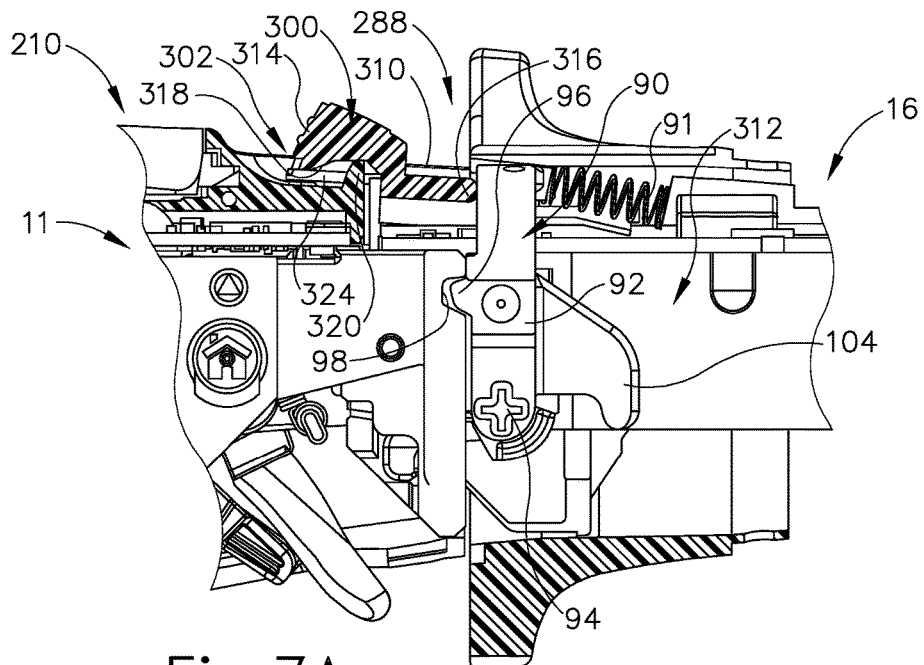
FIG. 7A depicts an enlarged cross-sectional side view of the instrument of FIG. 6, taken generally along a centerline of a shaft assembly, with a shaft assembly operatively coupled to a handle assembly.
Figure 7B:
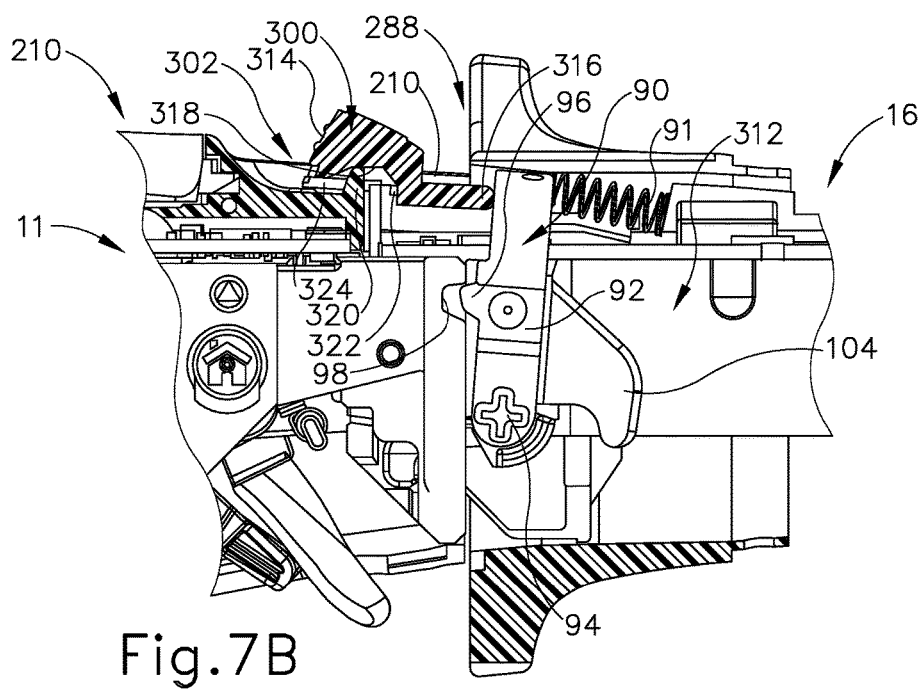
FIG. 7B depicts an enlarged cross-sectional side view of the instrument of FIG. 6, taken generally along a centerline of a shaft assembly, with the shaft assembly at a first stage of uncoupling from the handle assembly.
Figure 7C:
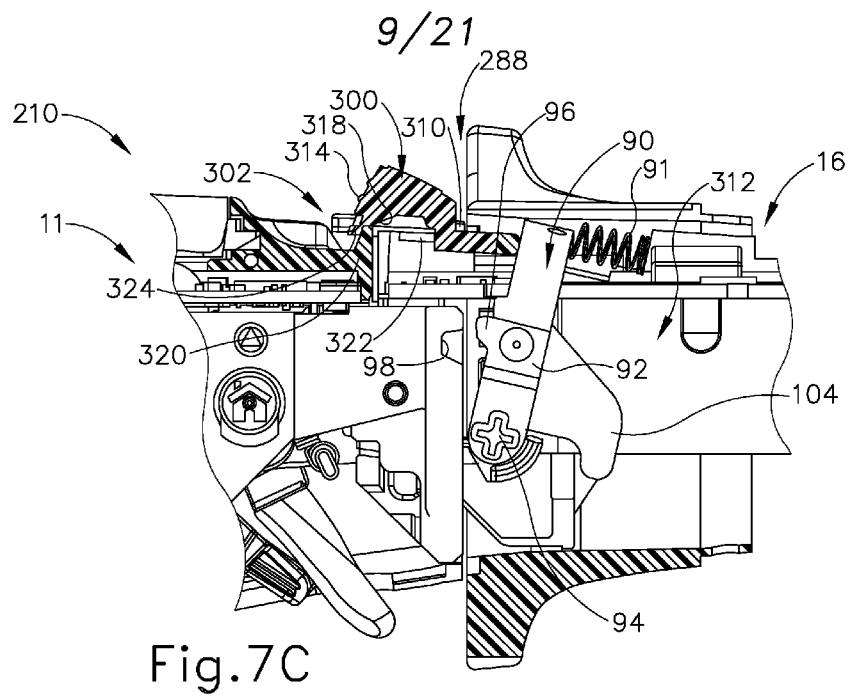
FIG. 7C depicts an enlarged cross-sectional side view of the instrument of FIG. 6, taken generally along a centerline of a shaft assembly, with the shaft assembly at a second stage of uncoupling from the handle assembly.

FIGS. 6-7C show exemplary surgical instrument (210), which includes handle assembly (11), shaft assembly (16), and ejection latch system (288) the configured to indicate the direction of removal along installation axis (IA) (see FIG. 2). Latch system (288) includes a latch actuator assembly (302) having a latch member in the form of a latch button (300) and a latch mount body (310). Latch mount body (310) is configured to slidably support latch button (300) while the operator manipulates latch button (300) between a locked position, a released position, and a removal position as shown respectively in FIGS. 7A-7C. Thereby, the operator slides latch button (300) distally from the locked position to the released position in order to operatively uncouple shaft assembly (16) from handle assembly (11). The operator then further slides latch button (300) distally from the released position to the removal position to urge the shaft assembly (16) toward the removal direction relative to the shaft assembly (16). While the description of the locked, released, and removal positions are detailed below as discrete positions, it will be appreciated that the operator may smoothly transition latch button (300) from the locked position to the released position and remove the shaft assembly (16) with a single, common motion; or via discrete manipulations as the operator so desires.

As shown in FIG. 7A, latch system (288) further includes a handle lock member in the form of distal attachment flange portion (78) and a shaft lock member in the form of lock yoke (90). As described above, lock yoke (90) is pivotally connected to chassis (64) at a proximal end portion (312) of shaft assembly (16) and biased proximally toward distal attachment flange portion (78). Upon operatively coupling shaft assembly (16) to handle assembly (11), pivot lugs (94) slide against distal attachment flange portion (78) and pivot lock yoke (90) about distal attachment flange portion (78) until grooves (98) capture the pivot lugs (94). Distal attachment flange portion (78) and lock yoke (90) thereby inhibit removal of shaft assembly (16) until the operator manipulates latch button (300).

To this end, latch button (300) includes an upper grip surface (314) and a distal nose (316) to pivot lock yoke (90) and free pivot lugs (94) from grooves (98). Upper grip surface (314) is textured so as to provide a surface by which the operator may effectively grip latch button (300). Distal nose (316) projects distally from upper grip surface (314) and extends to lock yoke (90). Latch button (300) further includes a lower ramp cam surface (318) that is configured to engage and slide along a cam base (320) that is rigidly attached to the handle assembly (11).

Latch mount body (310) is configured to enable latch button (300) to slide longitudinally and against cam base (320). In the present example, latch mount body (310) has a pair of opposing longitudinal latch slots (322) that slidably receive opposing ends of latch button (300). Latch mount body (310) also includes a hole (324) positioned such that lower ramp cam surface (318) contacts cam base (320) therethrough. As such, the engagement between lower ramp cam surface (318) and cam base (320) guides transverse movement of latch button (300), while latch button (300) is configured to longitudinally slide within each longitudinal latch slot (322) in latch mount body (310).

In use, FIG. 7A shows shaft assembly (16) operatively coupled with handle assembly (11) and latch button (300) in the locked position. In order to uncouple shaft and handle assemblies (16, 11), the operator grips upper grip surface (314) with a thumb or finger of a hand and slides latch button (300) distally toward the released position. In turn, the distal nose (316) engages lock yoke (90) and pivots lock yoke (90) distally to free pivot lugs (94). FIG. 7B shows shaft and handle assemblies (16, 11) operatively uncoupled with latch button (300) in the released position.

In the present example, shaft assembly (16) may be removed along the installation axis (IA) (see FIG. 2) from the released position, because shaft and handle assemblies (16, 11) are mechanically uncoupled at this stage. However, in order to indicate the direction of removal along the installation axis (IA), the operator further slides latch button (300) distally toward the release position shown in FIG. 7C. More particularly, as latch button (300) slides distally, lower ramp cam surface (318) slides transversely upwardly along cam base (320). Because latch button (300) is received within latch slots (322) of latch mount body (310), the upward movement of latch button (300) similarly urges the entirety of shaft assembly (16) upwardly in the removal direction along the installation axis (IA). In other words, latch system (288) partially ejects the shaft assembly (16) upwardly in the removal direction along the installation axis (IA) in response to further distal sliding of button (300). The operator, sensing this ejection through tactile feedback, may then continue to remove the shaft assembly (16) in the removal direction along the installation axis (IA) to complete removal of interchangeable shaft assembly (16) from handle assembly (11).

III. Surgical Instrument with Alternative Latch Systems

In some instances, it may be desirable to provide surgical instrument (10, 210) with an alternative form of latch system (88, 288). In particular, it may be desirable to provide surgical instrument (10, 210) with another ejection latch system (488) that includes a pivotable latch switch (500) that is configured to operatively uncouple the shaft and handle assemblies (16, 11) and indicate the direction of removal along the installation axis (IA) (see FIG. 2). In addition, it may also be desirable to provide the surgical instrument (10, 210) with a non-ejection latch system (688) that includes a pivotable latch switch (700) that does not urge or otherwise eject the shaft assembly (16) from the handle assembly (11). Various examples of alternative latch systems (488, 688) are described in greater detail below; while further examples will be apparent to those of ordinary skill in the art in view of the teachings herein. It should be understood that the various latch systems described below may be readily incorporated into surgical instrument (10, 210) in place of respective latch systems (88, 288). As such, like numbers below continue to indicate like features described above.

A. Exemplary Alternative Ejection Latch System with a Latch Switch

FIGS. 8A-10C show another exemplary surgical instrument (410), which includes handle assembly (11), shaft assembly (16), and ejection latch system (488) that is configured to indicate the direction of removal along installation axis (IA) (see FIG. 2). Latch system (488) includes a latch actuator assembly (502) having a latch member in the form of a latch switch (500) and a latch mount body (510). Latch mount body (510) is configured to pivotally support latch switch (500) while the operator manipulates latch switch (500) between a locked position, a released position, and a removal position as shown respectively in FIGS. 8A-8C and FIGS. 10A-10C. Thereby, the operator pivots latch switch (500) distally from the locked position to the released position in order to operatively uncouple shaft assembly (16) from handle assembly (11). The operator then further pivots latch switch (500) distally from the released position to the removal position to urge the shaft assembly (16) toward the removal direction relative to the shaft assembly (16). While the description of the locked, released, and removal positions are detailed below as discrete positions, it will be appreciated that the operator may smoothly transition latch switch (500) from the locked position to the released position and remove the shaft assembly (16) with a single, common motion; or via discrete manipulations as the operator so desires.

Figure 8A:
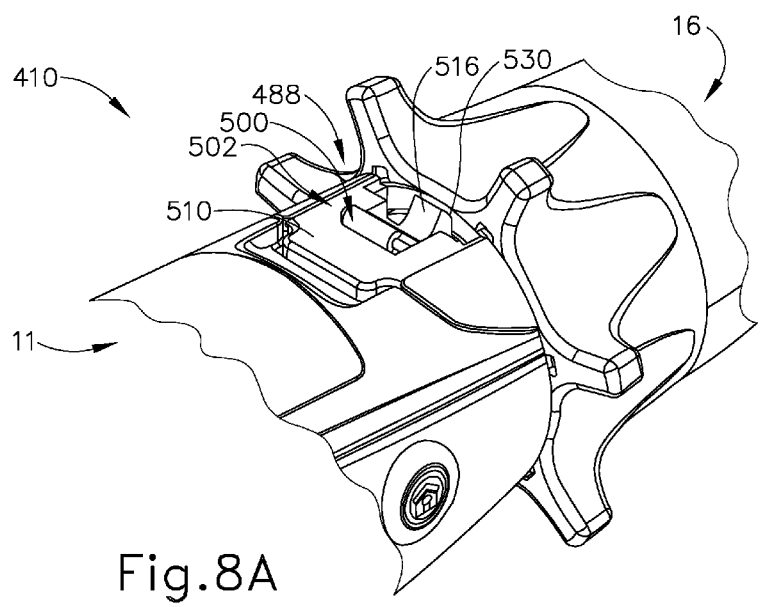
FIG. 8A depicts an enlarged rear perspective view of another exemplary surgical stapling instrument, with a shaft assembly operatively coupled to a handle assembly.
Figure 10A:
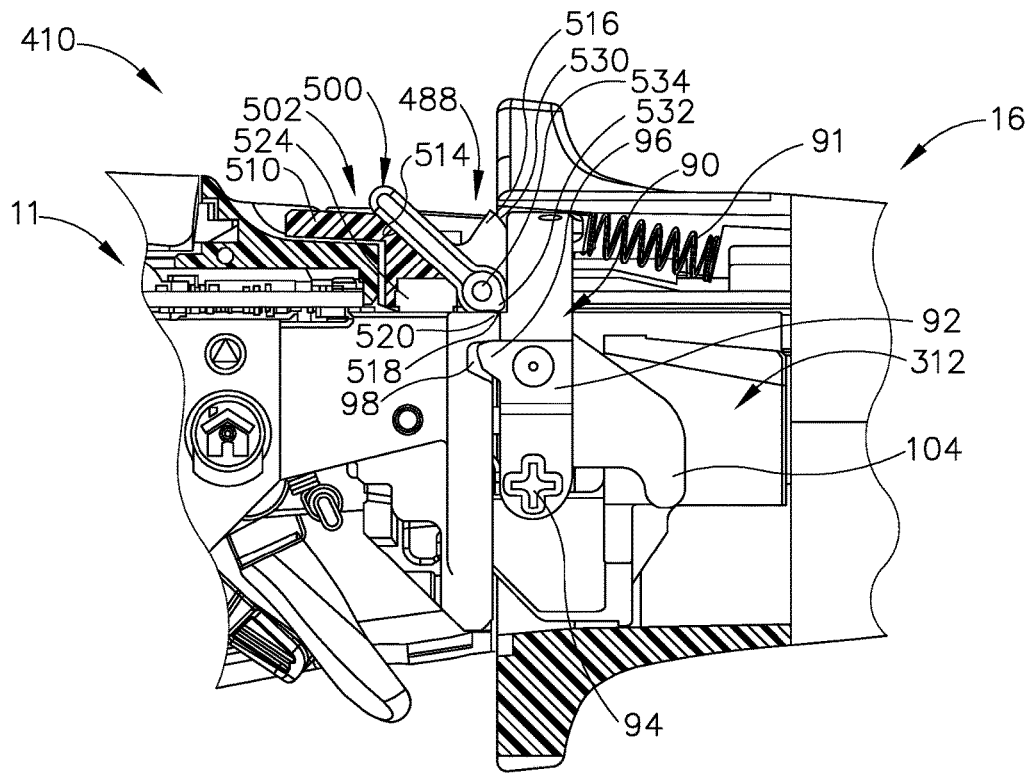
FIG. 10A depicts an enlarged cross-sectional side view of the instrument of FIG. 8A, taken generally along a centerline of the shaft assembly, with the shaft assembly operatively coupled to the handle assembly.

As shown in FIGS. 8A and 10A, latch system (488) further includes a handle lock member in the form of distal attachment flange portion (78) and a shaft lock member in the form of lock yoke (90). Latch button (500) includes a proximal grip surface (514) and a distal nose (516) to pivot lock yoke (90) and free pivot lugs (94) from grooves (98). Distal nose (516) projects distally from proximal grip surface (314) and extends to lock yoke (90). In the present example, distal nose (516) further includes an arcuate cam surface (530) that is configured to engage and pivot against lock yoke (90) for directing lock yoke (90) distally. Latch switch (500) further includes a pair of cam lobes (532), each having a cam lobe surface (518) that is configured to engage and pivot along a cam base (520) rigidly attached to the handle assembly (11).

Latch mount body (510) is configured to enable latch switch (500) to pivot longitudinally and against cam base (520). In the example shown in FIGS. 9 and 10A, latch mount body (510) has a pair of opposing lateral latch slots (522) that pivotally receive opposing ends of latch switch (500). More particularly, latch switch (500) includes coaxial and opposing lateral shafts (534) pivotally received within respective latch slots (522). Each of the lateral shafts (534) also respectively includes cam lobe (532) extending therefrom toward cam base (520). Latch mount body (510) also includes a hole (524) positioned such that each cam lob surface (518) contacts cam base (520) therethrough. As such, the engagement between each cam lobe surface (518) and cam base (520) guides transverse movement of latch switch (500), while latch switch (500) is configured to pivot within lateral latch slots (522) in latch mount body (510).

Figure 8B:
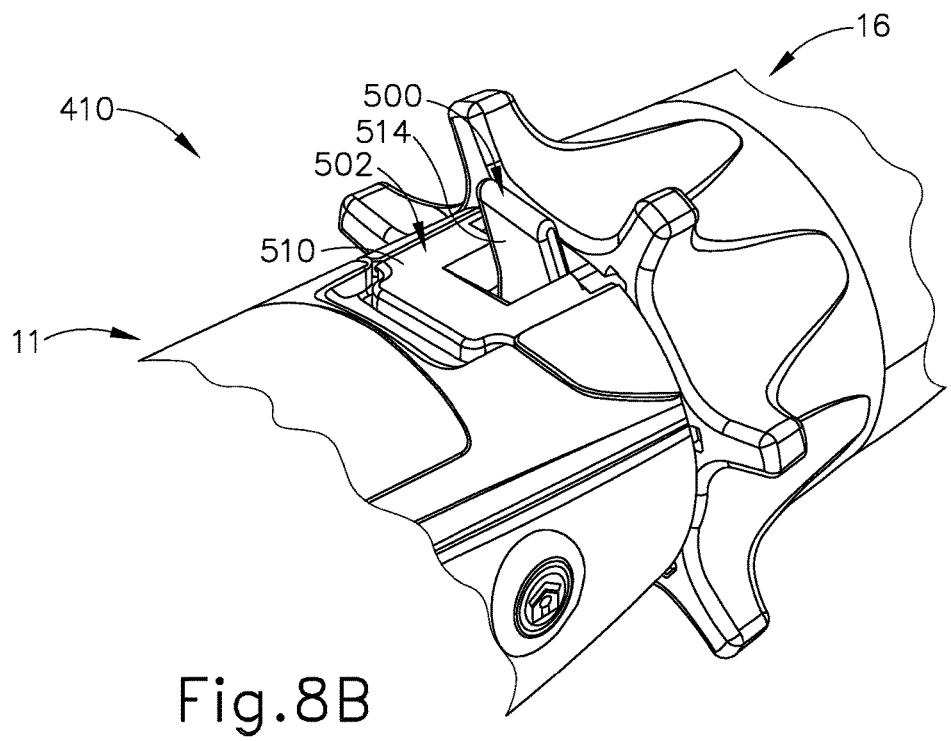
FIG. 8B depicts an enlarged rear perspective view of the instrument of FIG. 8A, with the shaft assembly at a first stage of uncoupling from the handle assembly.
Figure 8C:
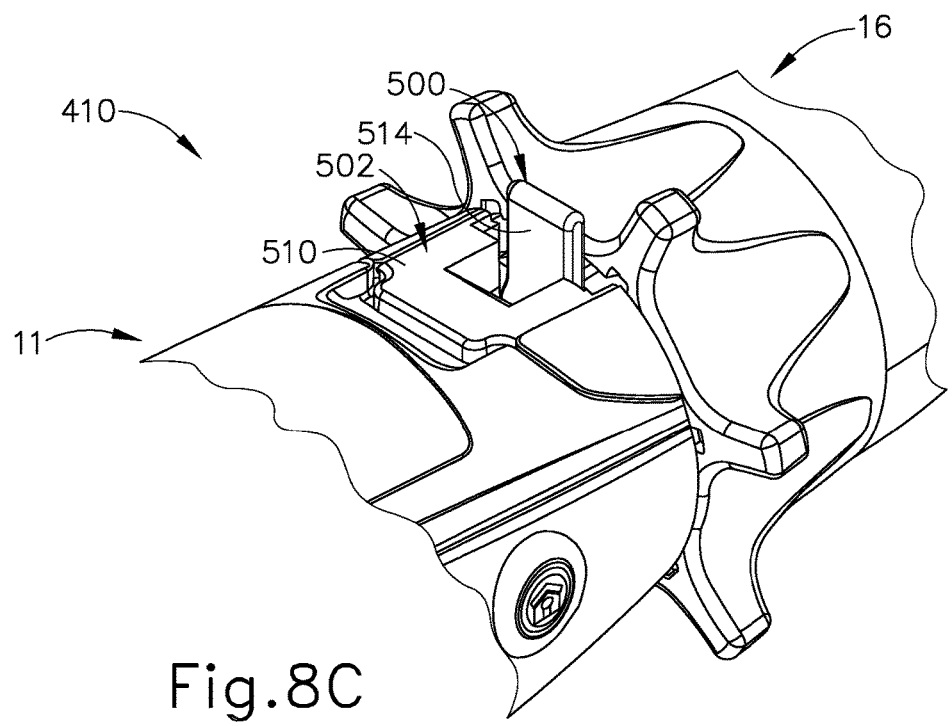
FIG. 8C depicts an enlarged rear perspective view of the instrument of FIG. 8A, with the shaft assembly at a second stage of uncoupling from the handle assembly.
Figure 9:
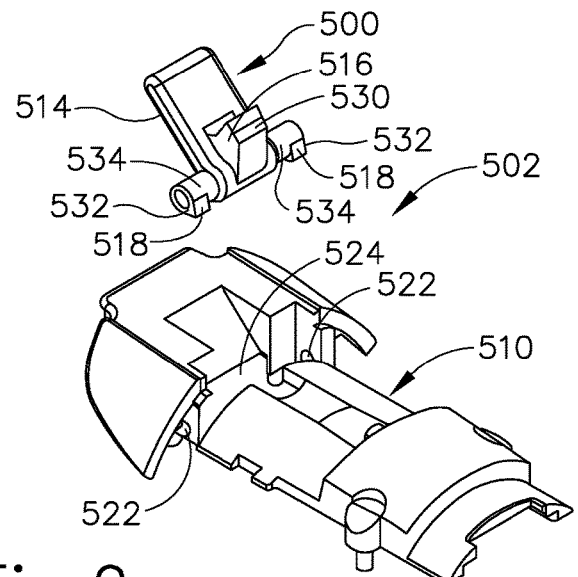
FIG. 9 shows an exploded perspective view of a portion of a latch system of the instrument of FIG. 8A.
Figure 10B:
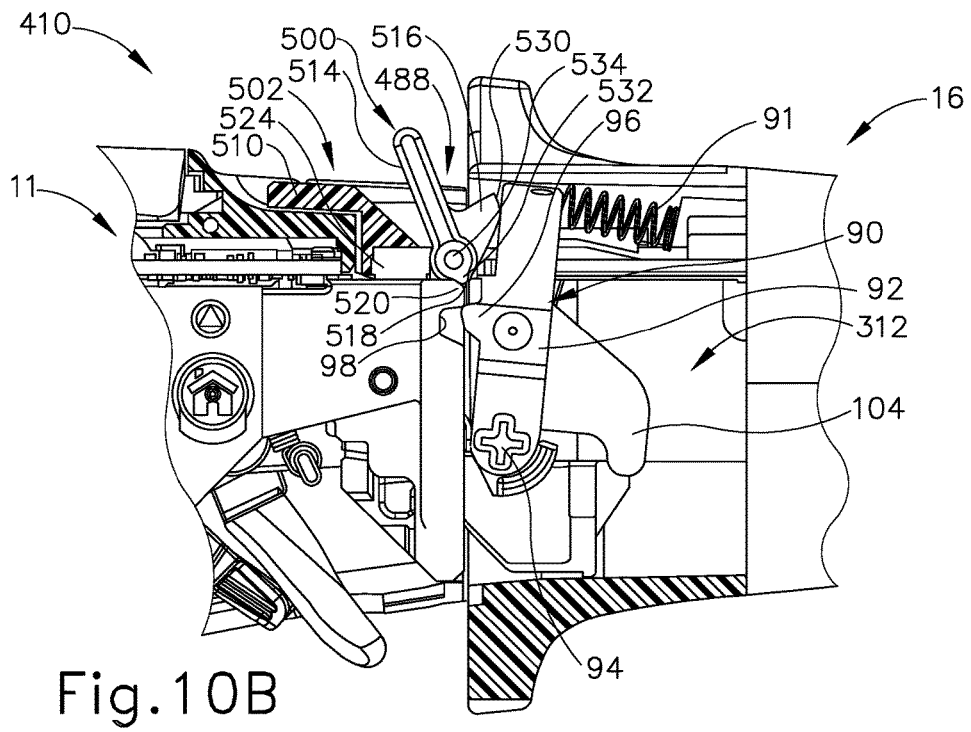
FIG. 10B depicts an enlarged cross-sectional side view of the instrument of FIG. 8A, taken generally along a centerline of a shaft assembly, with the shaft assembly at the first stage of uncoupling from the handle assembly.
Figure 10C:
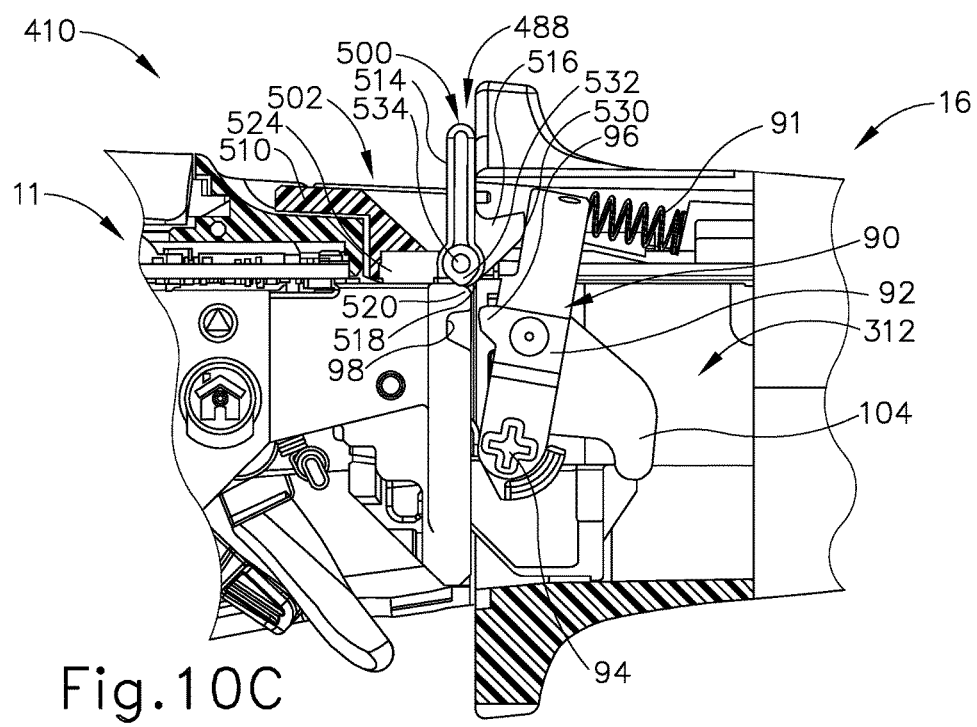
FIG. 10C depicts an enlarged cross-sectional side view of the instrument of FIG. 8A, taken generally along a centerline of a shaft assembly, with the shaft assembly at the second stage of uncoupling from the handle assembly.

In use, FIGS. 8A and 10A show shaft assembly (16) operatively coupled with handle assembly (11) and latch switch (500) in the locked position. In order to uncouple shaft and handle assemblies (16, 11), the operator grips proximal grip surface (514) with a thumb or finger of a hand and pivots latch switch (500) distally toward the released position. In turn, arcuate cam surface (530) of distal nose (516) engages lock yoke (90) and pivots lock yoke (90) distally to free pivot lugs (94). FIGS. 8B and 10B show shaft and handle assemblies (16, 11) operatively uncoupled with latch switch (500) in the released position.

In the present example, shaft assembly (16) may be removed along the installation axis (IA) (see FIG. 2) from the released position, because shaft and handle assemblies (16, 11) are mechanically uncoupled at this stage. However, in order to indicate the direction of removal along the installation axis (IA), the operator further pivots latch switch (500) distally toward the release position shown in FIGS. 8C and 10C. More particularly, as latch switch (500) pivots distally, each cam lobe surface (518) pivots about cam base (520) and directs lateral shafts (534) of latch switch (500) upwardly. Because latch switch (500) is received within latch slots (522) of latch mount body (510), the upward movement of latch switch (500) similarly urges the entirety of shaft assembly (16) upwardly in the removal direction along the installation axis (IA). In other words, latch system (488) partially ejects the shaft assembly (16) upwardly in the removal direction along the installation axis (IA) in response to further pivoting of latch switch (500). The operator, sensing this ejection through tactile feedback, may then continue to remove the shaft assembly (16) in the removal direction along the installation axis (IA) to complete removal of interchangeable shaft assembly (16) from handle assembly (11).

B. Exemplary Alternative Non-Ejection Latch System with a Latch Switch

FIGS. 11A-12B show another exemplary surgical instrument (610), which includes non-ejection latch system (688) having a latch switch (700) that is configured to uncouple the handle and shaft assemblies (16, 11) without indicating the direction of removal along installation axis (IA) (see FIG. 2). Latch system (688) includes a latch actuator assembly (702) having a latch member in the form of the latch switch (700) and a latch mount body (510). Latch mount body (510) is configured to pivotally support latch switch (700) while the operator manipulates latch switch (700) from a locked position to a released position as shown respectively in FIGS. 11A-11B and FIGS. 12A-12B. Thereby, the operator pivots latch switch (700) distally from the locked position to the released position in order to operatively uncouple shaft assembly (16) from handle assembly (11).

Generally, latch switch (700) operates like latch switch (500) (see FIGS. 10A-B) from the locked position to the released position. However, latch switch (700) does not include cam lobes (532) and cooperating cam base (520) for urging the shaft assembly (16) in the removal direction along installation axis (IA). Rather, latch system (688) relies on the intuitive feel of the latch switch (700) to indicate to the operator the removal direction along installation axis (IA).

Figure 11A:
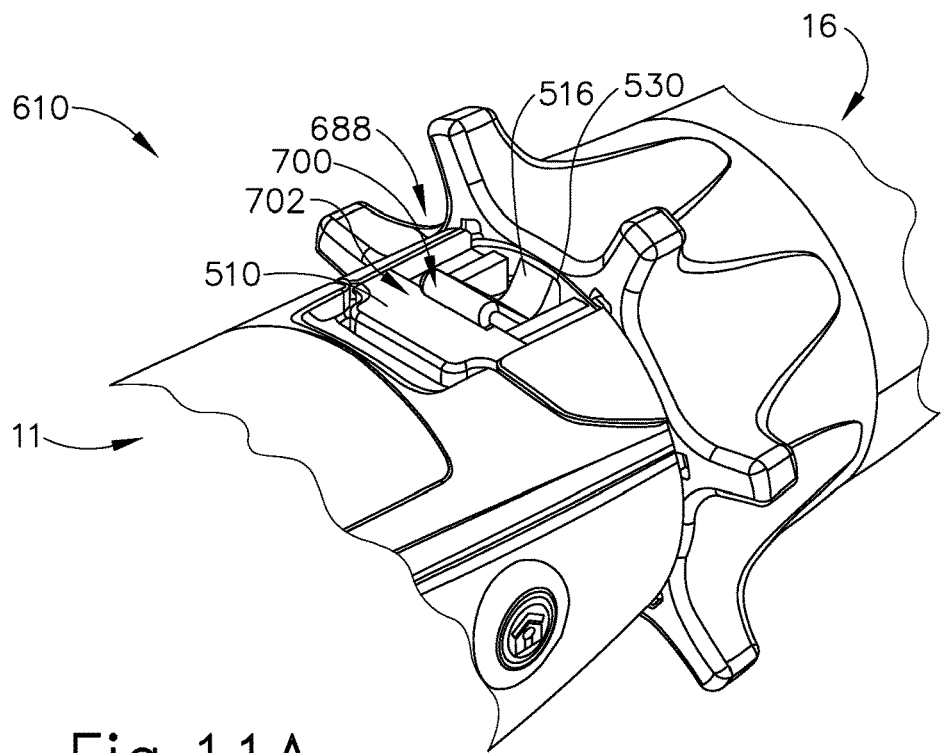
FIG. 11A depicts an enlarged rear perspective view of another exemplary surgical stapling instrument, with a shaft assembly operatively coupled to a handle assembly.
Figure 11B:
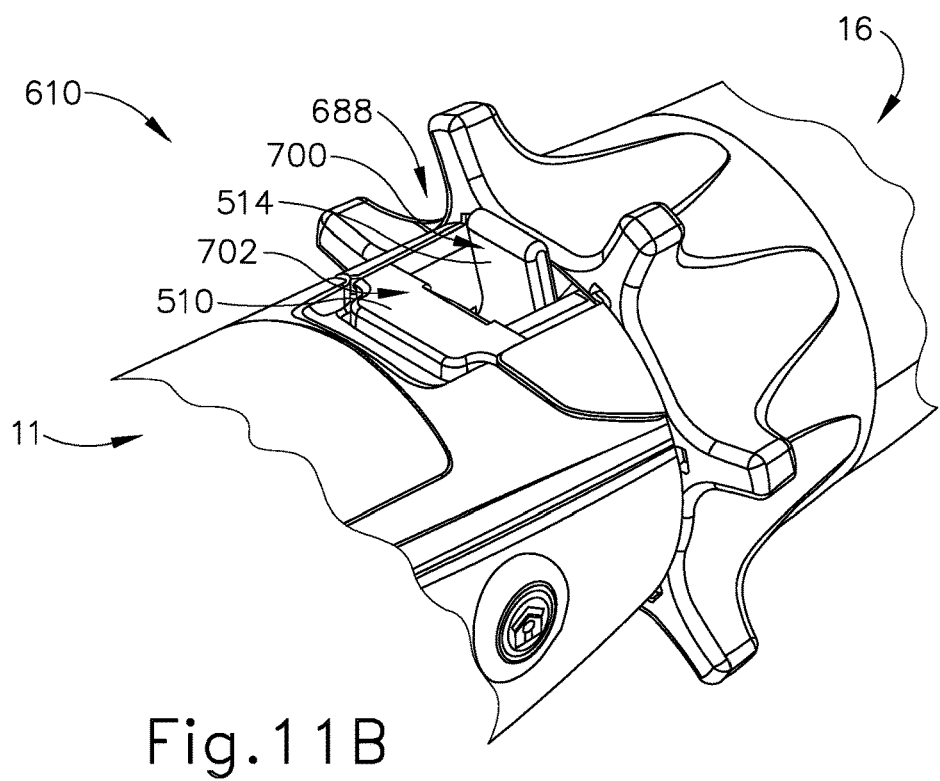
FIG. 11B depicts an enlarged rear perspective view of the instrument of FIG. 11A, with the shaft assembly at an initial stage of uncoupling from the handle assembly.
Figure 12A:
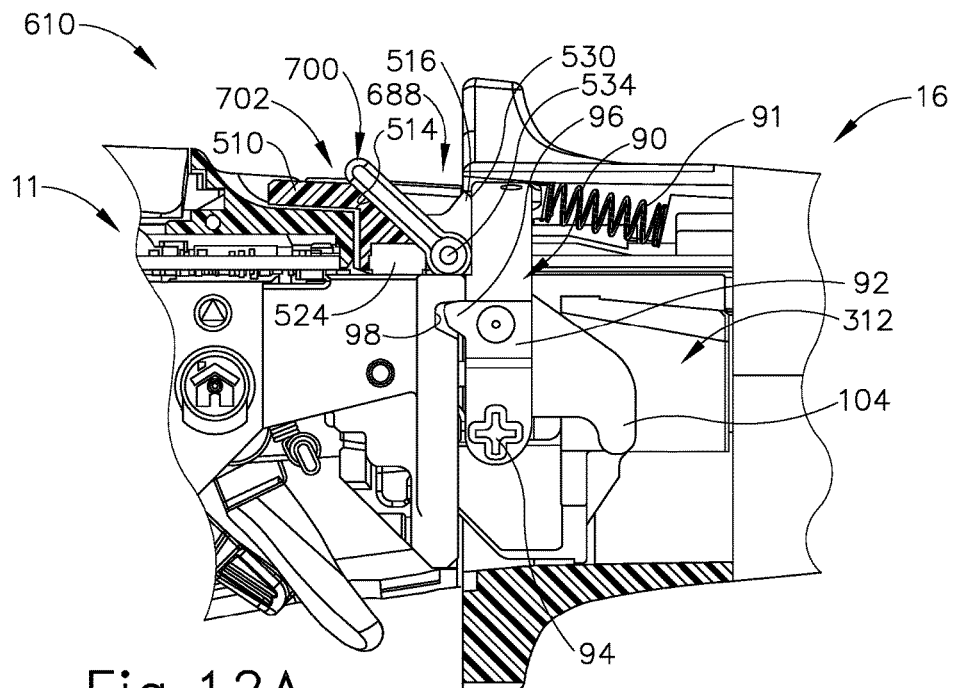
FIG. 12A depicts an enlarged cross-sectional side view of the instrument of FIG. 11A, taken generally along a centerline of the shaft assembly, with the shaft assembly operatively coupled to the handle.
Figure 12B:
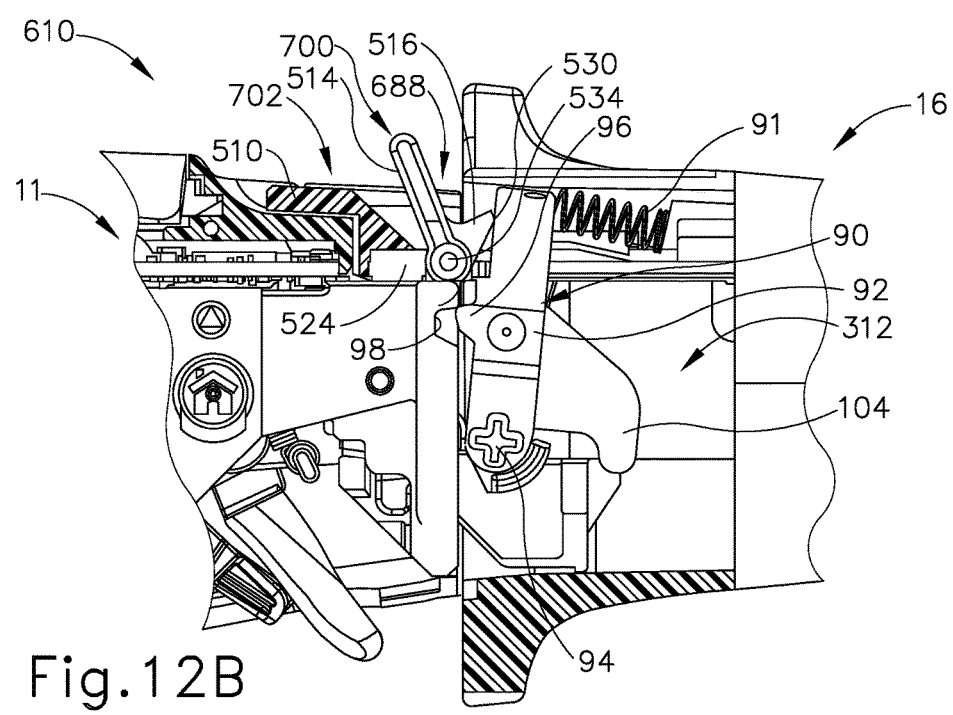
FIG. 12B depicts an enlarged cross-sectional side view of the instrument of FIG. 11A, taken generally along a centerline of the shaft assembly, with the shaft assembly at the initial stage of uncoupling from the handle assembly.

In use, FIGS. 11A and 12A show shaft assembly (16) operatively coupled with handle assembly (11) and latch switch (700) in the locked position. In order to uncouple shaft and handle assemblies (16, 11), the operator grips proximal grip surface (514) with a thumb or finger of a hand and pivots latch switch (500) toward the released position. In turn, arcuate cam surface (530) of distal nose (516) engages lock yoke (90) and pivots lock yoke (90) distally to free pivot lugs (94). FIGS. 11B and 12B show shaft and handle assemblies (16, 11) operatively uncoupled with latch switch (500) in the released position. From the released position, the operator simply directs shaft assembly (16) in the removal direction along installation axis (IA) to complete removal of interchangeable shaft assembly (16) from handle assembly (11).

IV. Surgical Instrument with a Shaft Assembly in Data Communication with a Handle Assembly In some instances, it may be desirable to provide surgical instrument (10, 210, 410, 610) with hardware and software that are configured to communicate data from shaft assembly (16) to handle assembly (11). In particular, it may be desirable to set handle assembly (11) with a predetermined clinical function that is unique to the particular kind of interchangeable shaft assembly (16) that happens to be coupled with handle assembly (11). Thereby, handle assembly (11) may be used in a variety of predetermined clinical functions respectively unique to a variety of kinds of shaft assemblies (not shown). An example of such a surgical instrument (810) is described in greater detail below; while further examples will be apparent to those of ordinary skill in the art in view of the teachings herein. It should be understood that the hardware and any associated software described below may be readily incorporated into surgical instrument (10, 210, 410, 610). As such, like numbers below indicate like features described above.

Figure 13:
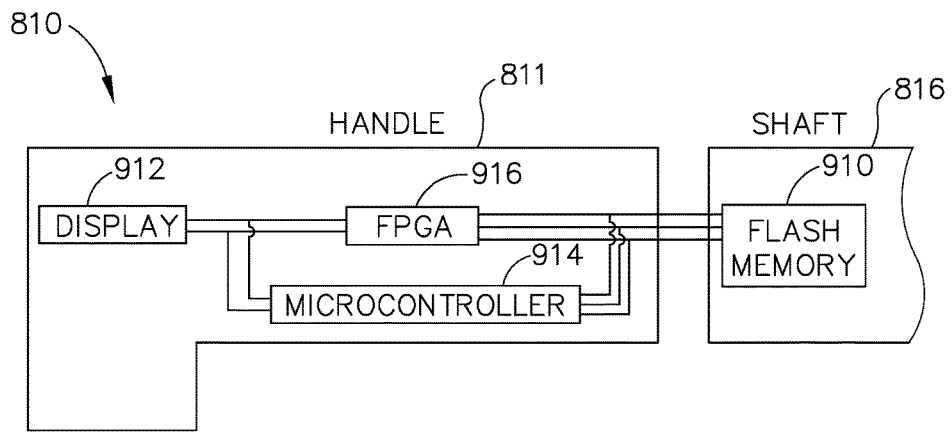
FIG. 13 depicts a schematic diagram of an exemplary surgical stapling instrument having Field Programmable Gate Array configured receive core logic from a Flash Memory upon operatively coupling a shaft assembly to a handle assembly.
Figure 14:
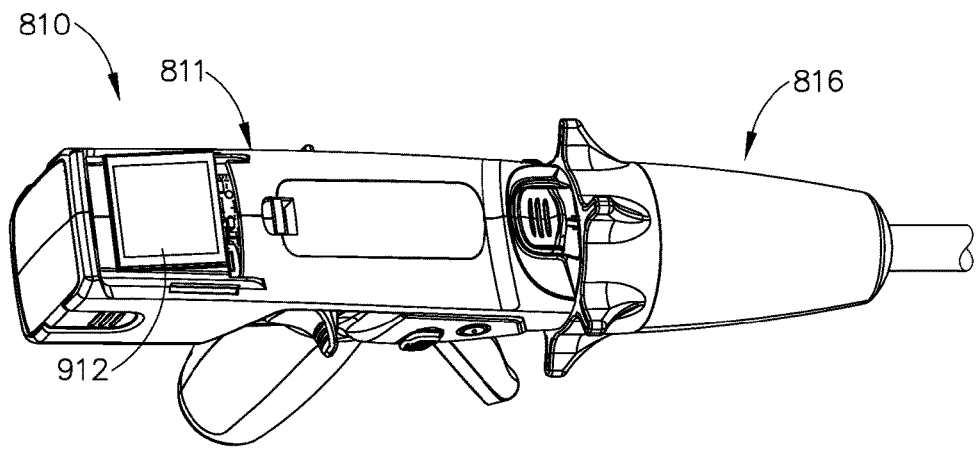
FIG. 14 depicts a top perspective view of the handle assembly of the instrument of FIG. 13.
Figure 15:
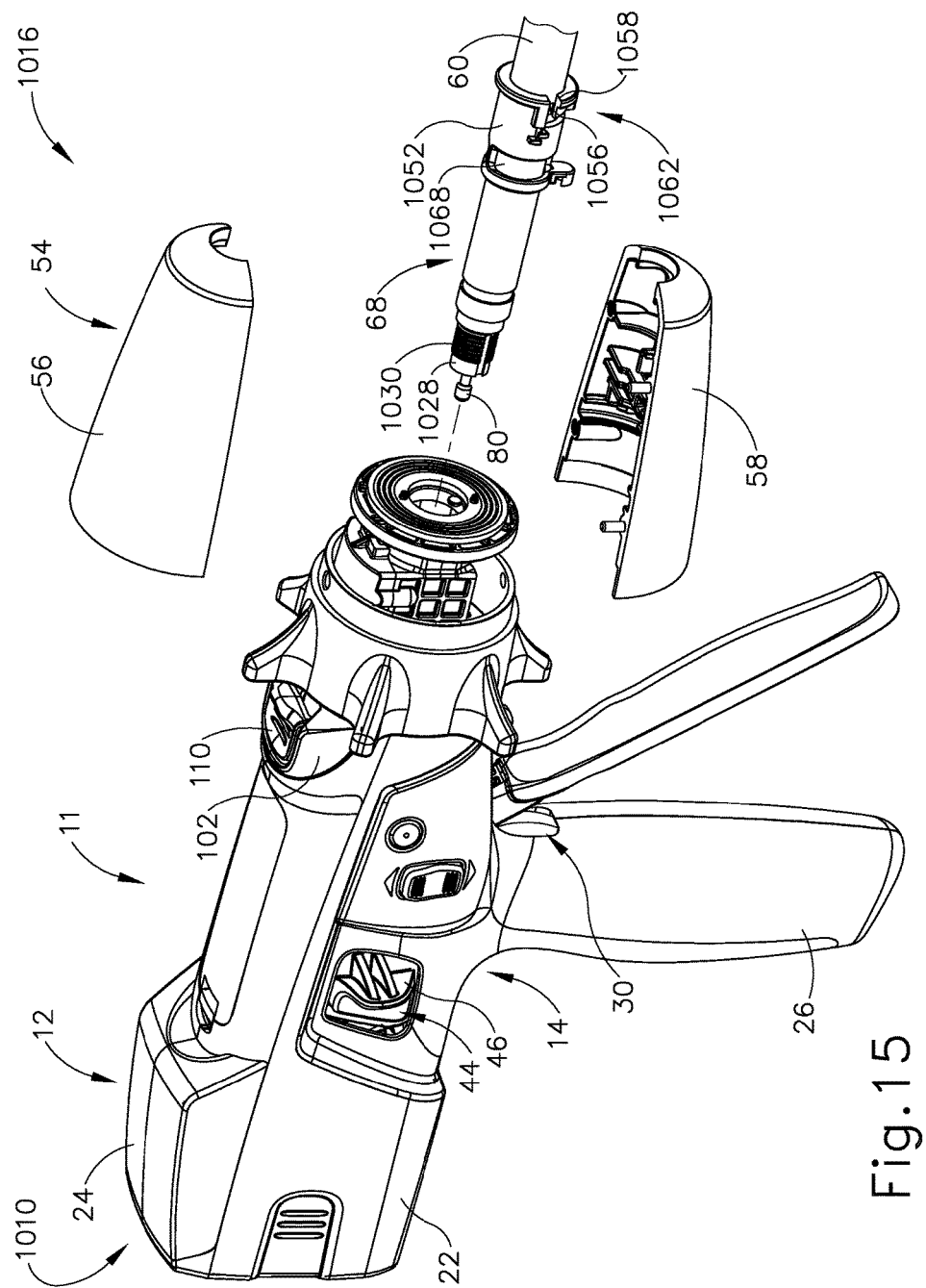
FIG. 15 depicts a partially exploded perspective view of another exemplary surgical stapling instrument having a shaft assembly that includes a shifter mechanism.
Figure 16:
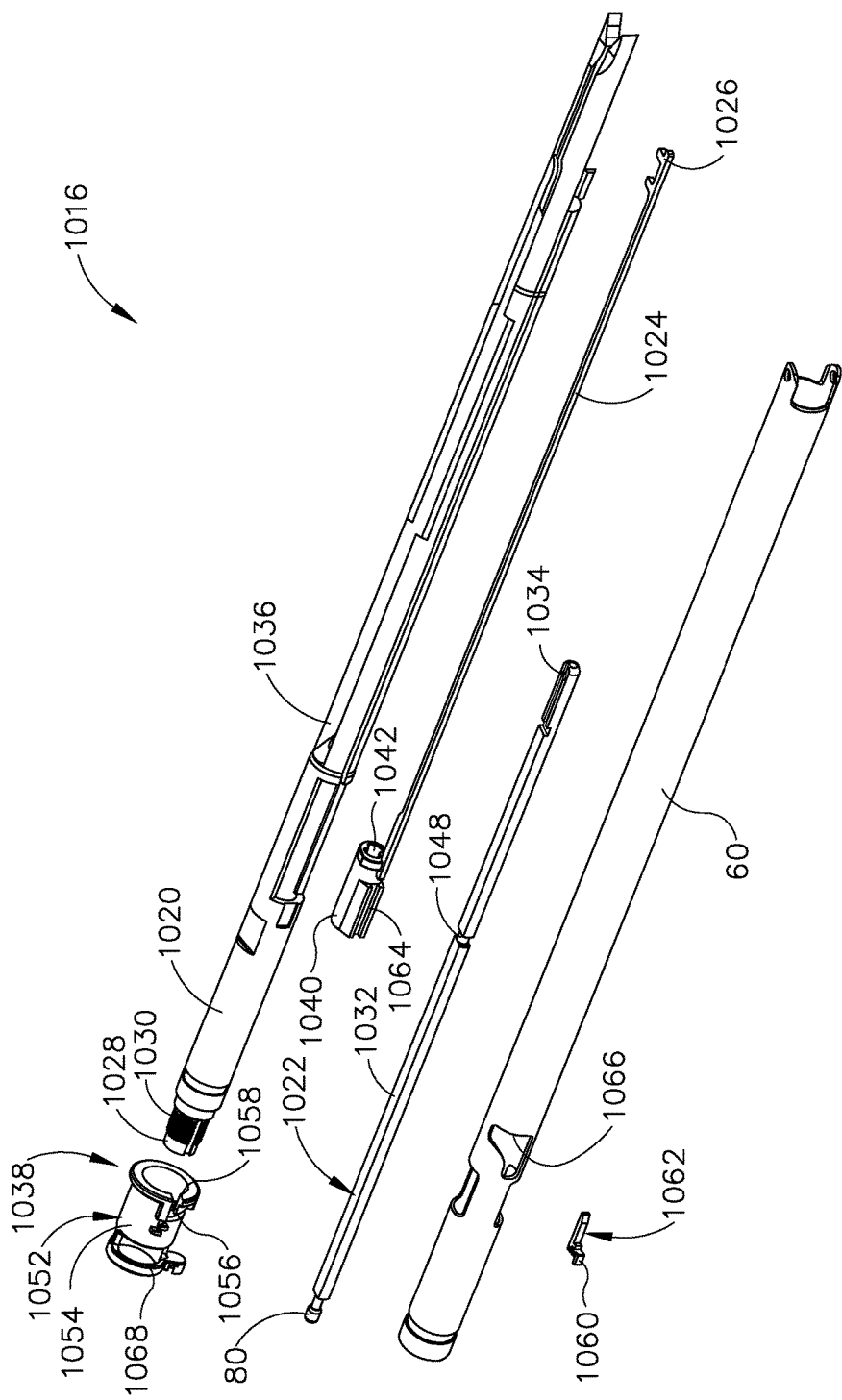
FIG. 16 depicts an exploded perspective view of the shaft assembly of FIG. 15.
Figure 17:
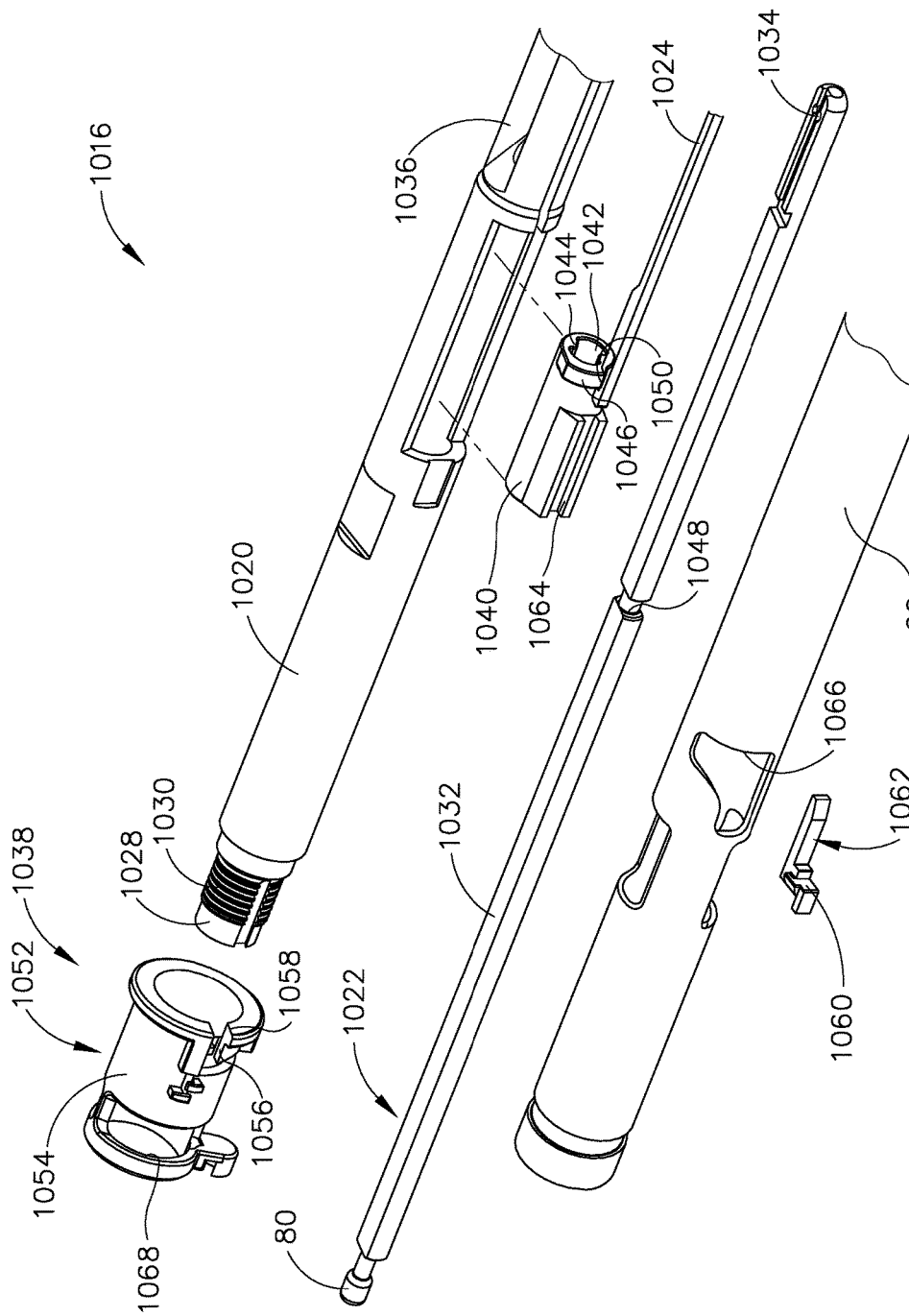
FIG. 17 depicts an enlarged exploded perspective view of the shaft assembly of FIG. 16 in a first state of assembly.
Figure 18:
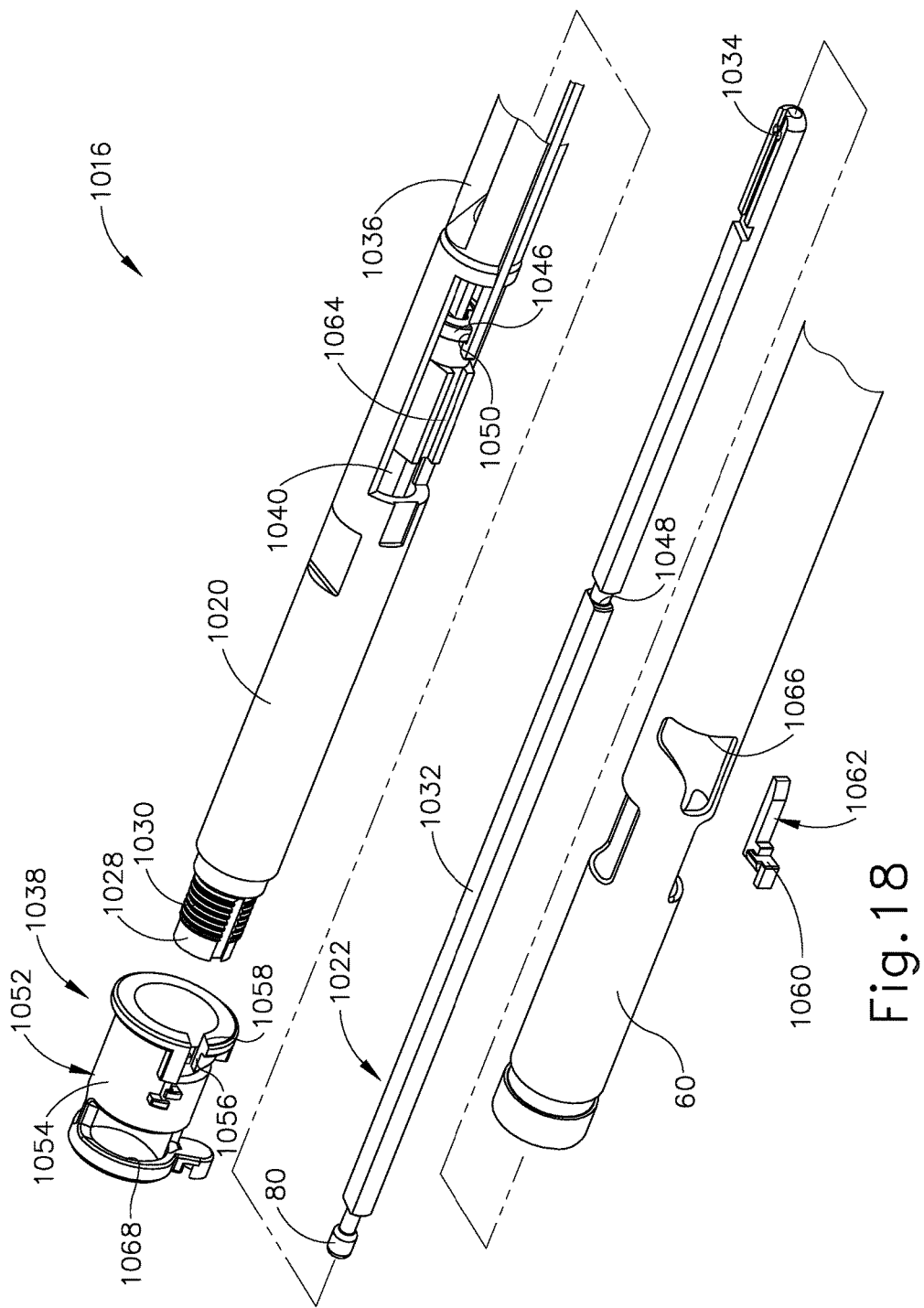
FIG. 18 depicts an enlarged, partially exploded perspective view of the shaft assembly of FIG. 17 in a second state of assembly.

FIGS. 13-14 show one example of surgical instrument (810) that is configured to communicate data, such as software and/or operation parameters, from a shaft assembly (816) to a handle assembly (811). Shaft assembly (816) includes a memory, such as a flash member (910) that is configured to store the data such as software and/or operation parameters that are particularly associated with that particular kind of shaft assembly (816). Handle assembly (811) includes a display (912), a microcontroller (914), and a field-programmable gate array (916). As shaft assembly (816) operatively couples with handle assembly (811), field-programmable gate array (916) and microcontroller (914) electrically connect in parallel between display (912) and flash member (910).

Microcontroller (914) includes basic functional code for general operation of handle assembly (811), whereas field-programmable gate array (916) is generally blank and readily programmable. In this example, microcontroller (914) does not include the data such as software and/or operation parameters that are particularly associated with a particular kind of shaft assembly (816). Instead, microcontroller (914) includes data such as software and/or operation parameters that are generally associated with various kinds of shaft assemblies (816). In use, microcontroller (914) guides user operation of handle assembly (811), such as by providing instructions to the operator via display (912). The operator, in preparation for operating shaft assembly (816) operatively couples shaft assembly (816) to handle assembly (811), as shown in FIGS. 13-14. Upon operative coupling, microcontroller (914) facilitates communication and transfer of data from flash memory (910) and into field-programmable gate array (916) such that handle assembly (811) is then configured to perform the predetermined clinical function that is specifically associated with that particular kind shaft assembly (816).

In other words, handle assembly (811) contains no data such as software and/or operation parameters that are particularly associated with a particular kind of shaft assembly (816) until a shaft assembly (816) is fully coupled with handle assembly (811). Shaft assembly (816) is the component that permanently stores the data such as software and/or operation parameters that are particularly associated with that particular kind of shaft assembly (816). This data (i.e., software and/or operation parameters that are particularly associated with that particular kind of shaft assembly (816)) is automatically transferred to field-programmable gate array (916) when shaft assembly (816) is fully coupled with handle assembly (811). When instrument (810) is used thereafter (while the same shaft assembly (816) is fully coupled with handle assembly (811)), the software and/or operation parameters that are particularly associated with that particular kind of shaft assembly (816) are executed from field-programmable gate array (916). It should therefore be understood that field-programmable gate array (916) provides a blank slate for each shaft assembly (816) that is coupled with handle assembly (811), such that handle assembly (811) does not need to permanently story software and/or operation parameters that are particularly associated with certain kinds of shaft assemblies (816). Handle assembly (811) only needs to store data such as software and/or operation parameters that are common among various kinds of shaft assemblies (816). This may make handle assembly (811) more readily adaptable to new and different kinds of shaft assemblies (816).

It should further be understood that the data such as software and/or operation parameters that are transferred from flash memory (910) to field-programmable gate array (916) may include the full logical operation parameters of shaft assembly (816), not just a simple hardware definition. In other words, the full clinical function of handle assembly (811) may be updated or modified by flash memory (910) of shaft assembly (816).

V. Surgical Instrument with an Alternative Shaft Assembly

It may also be desirable to provide surgical instrument (10, 210, 410, 610, 810) with an alternative shaft assembly (1016) that is configured to provide improved assembly. An example of such a surgical instrument (1010) having shaft assembly (1016) is described in greater detail below; while further examples will be apparent to those of ordinary skill in the art in view of the teachings herein. It should be understood that the shaft assembly (1016) described below may be readily incorporated into surgical instrument (10, 210, 410, 610). As such, like numbers below indicate like features described above.

As can be seen in FIGS. 15-19, surgical instrument (1010) includes interchangeable shaft assembly (1016) and handle assembly (11). Shaft assembly (1016) includes a spine (1020) that is configured to fixedly support a shaft frame portion (not shown) of articulation lock (not shown). Spine (1020) is also configured to slidably support a firing member (1022) therein. In addition, spine (1020) is configured to slidably support closure tube (60), which extends around spine (1020). Spine (1020) is also configured to slidably support a proximal articulation driver (1024). Articulation driver (1024) has a distal end (1026) that is configured to operatively engage the articulation lock (not shown). As indicated above, the articulation lock (not shown) and articulation frame (not shown) may be constructed and operable in accordance with at least some of the teachings of U.S. Pub. No. 2014/0263541, now abandoned, the disclosure of which is incorporated by reference herein.

In the present example, spine (1020) has a proximal end (1028) that is rotatably supported in chassis (64) (see FIG. 5A). In particular, proximal end (1028) of spine (1020) has a thread (1030) formed thereon for threaded attachment to a spine bearing (not shown) that is configured to be supported within chassis (64) (see FIG. 5A). Such an arrangement facilitates rotatable attachment of spine (1020) such that spine (1020) may be selectively rotated about the longitudinal axis of shaft assembly (16) relative to chassis (64).

A Firing member (1022) is supported for axial travel within spine (1020). Firing member (1022) includes an intermediate firing shaft portion (1032) that is configured for attachment to a distal cutting portion of a knife bar (not shown). Firing shaft portion (1032) includes a longitudinal slot (1034) in the distal end thereof that is configured to receive distal knife bar (not shown). Spine (1020) also has an elongate opening or window (1036) therein to facilitate assembly and insertion of intermediate firing shaft portion (1032) into shaft frame (not shown). Firing member (1022) may be further configured and operable in accordance with at least some of the teachings of U.S. Pub. No. 2014/0263541, now abandoned, the disclosure of which is incorporated by reference herein.

Further to the above, shaft assembly (1016) includes a clutch assembly (1038) that is operable to selectively and releasably couple the articulation driver (1024) to firing member (1022). In the present example, clutch assembly (1038) includes a lock collar, or sleeve (1040), that is positioned around firing member (1022). Lock sleeve (1040) can be rotated between an engaged position in which lock sleeve (1040) couples articulation driver (1024) to firing member (1022); and a disengaged position in which articulation driver (1024) is not operatively coupled to firing member (1022). When lock sleeve (1040) is in its engaged position, distal movement of firing member (1022) can move articulation driver (1024) distally and, correspondingly, proximal movement of firing member (1022) can move articulation driver (1024) proximally. When lock sleeve (1040) is in its disengaged position, movement of firing member (1022) is not transmitted to articulation driver (1024) and, as a result, firing member (1022) can move independently of articulation driver (1024). It should therefore be understood that lock sleeve (1040) is rotatable to transition between an articulation drive mode and a firing drive mode. In various circumstances, articulation driver (1024) can be held in position by articulation lock (not shown) when articulation driver (1024) is not being moved in the proximal or distal directions by firing member (1022).

Lock sleeve (1040) includes a cylindrical, or an at least substantially cylindrical, body defining a longitudinal aperture (1042) defined therein configured to receive firing member (1022). Lock sleeve (1040) also includes diametrically-opposed, inwardly-facing lock protrusions (1044) and an outwardly-facing lock member (1046). Lock protrusions (1044) are configured to be selectively engaged with firing member (1022). More particularly, when lock sleeve (1040) is in its engaged position, lock protrusions (1044) are positioned within a drive notch (1048) defined in firing member (1022) such that a distal pushing force and/or a proximal pulling force is transmitted from firing member (1022) to lock sleeve (1040). When lock sleeve (1040) is in its engaged position, lock member (1046) is received within a drive notch (1050) defined in articulation driver (1024) such that the distal pushing force and/or the proximal pulling force applied to lock sleeve (1040) is transmitted to articulation driver (1024). In effect, firing member (1022), lock sleeve (1040), and articulation driver (1024) will move together when lock sleeve (1040) is in its engaged position.

On the other hand, when lock sleeve (1040) is in its disengaged position, lock protrusions (1044) are not positioned within drive notch (1048) of firing member (1022) and, as a result, a distal pushing force and/or a proximal pulling force is not transmitted from firing member (1022) to lock sleeve (1040). Correspondingly, the distal pushing force and/or the proximal pulling force is not transmitted to the articulation driver (1024). In such circumstances, firing member (1022) can be slid proximally and/or distally relative to lock sleeve (1040) and proximal articulation driver (1024).

Figure 19:
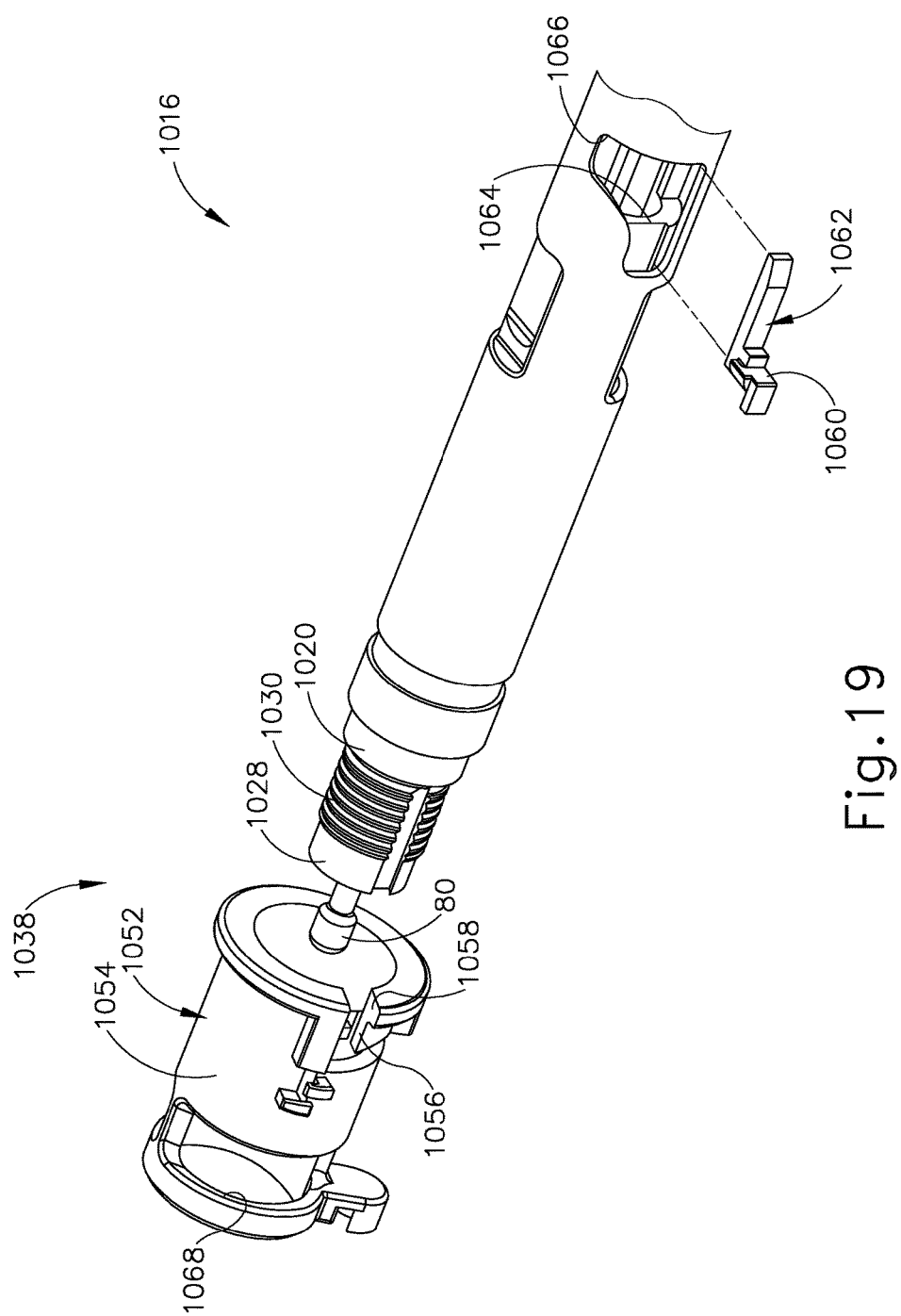
FIG. 19 depicts an enlarged, partially exploded perspective view of the shaft assembly of FIG. 17 in a third state of assembly.
Figure 20A:
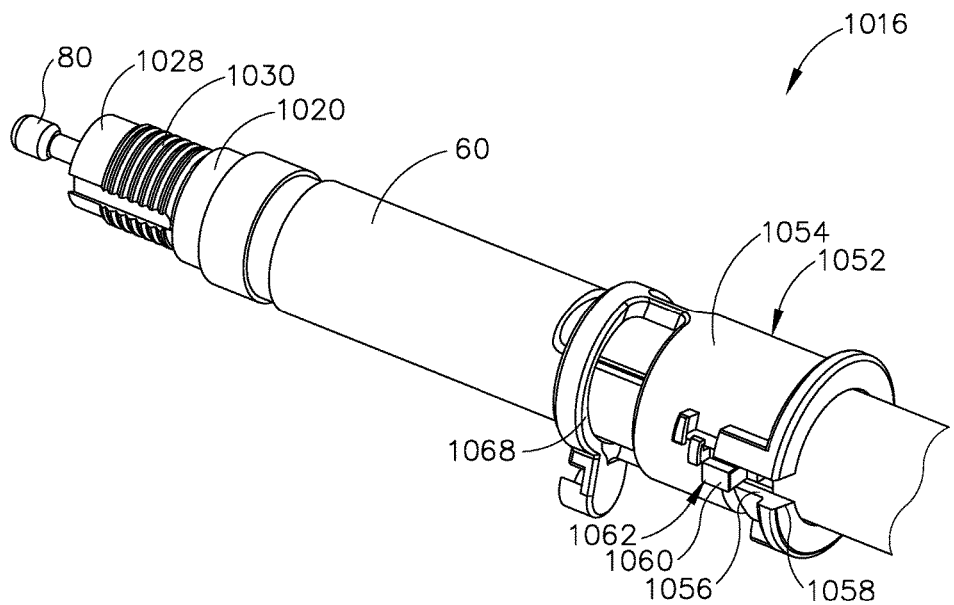
FIG. 20A depicts an enlarged perspective view of the shaft assembly of FIG. 16, with the shifter mechanism in a first engaged position.
Figure 20B:
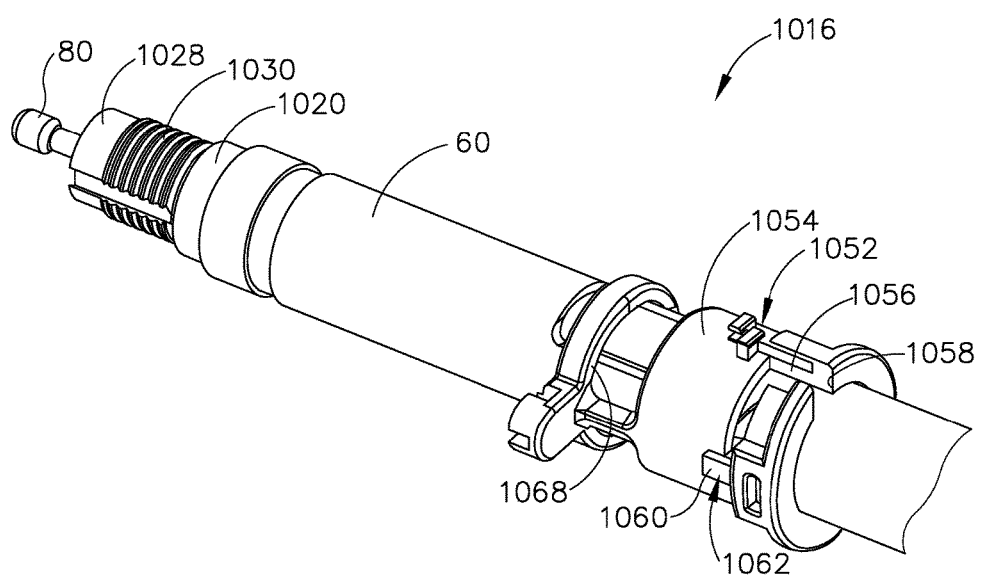
FIG. 20B depicts an enlarged perspective view of the shaft assembly of FIG. 16, with the shifter mechanism in a second engaged position.

Shaft assembly (1016) further includes a switch drum (1052) that is rotatably received on closure tube (60) as shown in greater detail in FIGS. 19-20. Switch drum (1052) includes a hollow shaft segment (1054) that has an L-shaped slot (1056) extending to a distal opening (1058) into the L-shaped slot (1056). The distal opening (1058) receives a transverse pin (1060) of a shifter plate (1062). In one example, shifter plate (1062) is received within a longitudinal slot (1064) provided in lock sleeve (1040) to facilitate axial movement of lock sleeve (1040) when engaged with articulation driver (1024). In addition, closure tube (60) includes an outer L-shaped slot (1066) through which shifter plate (1062) is inserted through for accessing longitudinal slot (1064) during installation. A rotary torsion spring (not shown) may be included to engage switch drum (1052) to rotatably bias switch drum (1052) relative to lock sleeve (1040). Switch drum (1052) also includes at least partially circumferential openings (1068) defined therein that can be configured to receive circumferential mounts (not shown) extending from nozzle halves (56, 58) and permit relative rotation, but not translation, between switch drum (1052) and proximal nozzle (54). Rotation of switch drum (1052) will ultimately result in the rotation of shifter plate (1062) and lock sleeve (1040) between its engaged and disengaged positions. Thus, in essence, nozzle (54) may be employed to operatively disengage and engage articulation drive system with firing drive system as respectively shown in FIGS. 20A and 20B.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a shaft assembly having a distal end portion and a proximal end portion, the proximal end portion including an end effector projecting distally therefrom; (b) a handle assembly configured to receive the proximal end portion of the shaft assembly; and (c) a latch system configured to operatively couple the shaft assembly to the handle assembly, the latch system including: (i) a shaft lock member connected to the shaft assembly, (ii) a handle lock member connected to the handle assembly, wherein the handle lock member is configured to engage the shaft lock member and inhibit the shaft assembly from operatively uncoupling from the handle assembly, (iii) a cam base, and (iv) a latch member, the latch member having a cam surface configured to engage the cam base, wherein the latch member is configured to selectively move from a locked position to a released position such that movement of the latch member toward the unlocked position is configured to cause the shaft lock member to disengage from the handle lock member and thereby operatively uncouple the shaft assembly from the handle assembly in the released position, wherein the latch member is further configured to selectively move from the released position to a removal position such that movement of the latch member toward the removal position is configured to cause the cam surface of the latch member to engage the cam base and thereby urge the shaft assembly in a removal direction relative to the handle assembly for indicating the removal direction to a user.

Example 2

The surgical instrument of Example 1, wherein the latch member is configured to engage at least one of the shaft and handle lock members and thereby cause the shaft lock member to disengage from the handle lock member as the latch member moves from the unlocked position toward the released position.

Example 3

The surgical instrument of Example 2, wherein the handle assembly includes the cam base and the shaft assembly includes the latch member.

Example 4

The surgical instrument of Example 3, wherein the latch member of the shaft assembly is configured to engage the shaft lock member and thereby cause the shaft lock member to disengage from the handle lock member as the latch member moves from the unlocked position toward the released position.

Example 5

The surgical instrument of Example 4, wherein the handle lock member is rigidly connected to the handle assembly and the shaft lock member is in the form of a shaft lock yoke pivotally connected to the shaft assembly, such that the shaft lock yoke is biased for engaging the handle lock member.

Example 6

The surgical instrument of any one or more of Examples 1 through 5, wherein the handle assembly includes the cam base and the shaft assembly includes the latch member, and the latch member comprises a latch button, wherein the latch button is slidably mounted to the proximal end portion of the shaft assembly such that the latch button is configured to slide from the locked position toward the removal position.

Example 7

The surgical instrument of Example 6 wherein the latch button includes a distal nose configured to engage the shaft lock member for disengagement from the handle lock member.

Example 8

The surgical instrument of any one or more of Examples 6 through 7, wherein the cam surface of the latch button is in the form of a lower ramp cam surface configured to transversely slide along the cam base to thereby urge the shaft assembly in the removal direction relative to the handle assembly.

Example 9

The surgical instrument of any one or more of Examples 6 through 8, wherein the latch system further includes a latch mount body rigidly connected to the proximal end portion thereof, the latch mount body configured to transversely capture the latch button while the latch button is configured to slide relative to the latch mount body from the locked position toward the removal position.

Example 10

The surgical instrument of Example 9, wherein the latch mount body includes a hole extending therethrough, and the hole is configured to provide for direct contact between the cam base and the cam surface of the latch button therethrough.

Example 11

The surgical instrument of any one or more of Examples 1 through 10, wherein the handle assembly includes the cam base and the shaft assembly includes the latch member, and the latch member comprises a latch switch, wherein the latch switch is pivotally mounted to the proximal end portion of the shaft assembly such that the latch switch is configured to pivot from the locked position toward the removal position.

Example 12

The surgical instrument of Example 11, wherein the latch switch includes a distal nose configured to engage the shaft lock member for disengagement from the handle lock member.

Example 13

The surgical instrument of any one or more of Examples 11 through 12, wherein the cam surface of the latch switch is in the form of a cam lobe surface configured to rotatably slide along the cam base to thereby urge the shaft assembly in the removal direction relative to the handle assembly.

Example 14

The surgical instrument of any one or more of Examples 11 through 13, wherein the latch system further includes a latch mount body rigidly connected to the proximal end portion thereof, the latch mount body configured to capture the latch switch such that the latch switch is configured to pivot relative to the latch mount body from the locked position toward the removal position.

Example 15

The surgical instrument of Example 14, wherein the latch mount body includes a hole extending therethrough, and the hole is configured to provide for direct contact between the cam base and the cam surface of the latch switch therethrough.

Example 16

A surgical instrument, comprising: (a) a shaft assembly having a distal end portion and a proximal end portion, the proximal end portion including an end effector projecting distally therefrom; (b) a handle assembly configured to receive the proximal end portion of the shaft assembly; and (c) a latch system configured to operatively couple the shaft assembly to the handle assembly, the latch system including: (i) a shaft lock member connected to the shaft assembly, (ii) a handle lock member connected to the handle assembly, wherein the handle lock member is configured to engage the shaft lock member and inhibit the shaft assembly from operatively uncoupling from the handle assembly, and (iii) a latch switch configured to selectively pivot from a locked position to a released position such that movement of the latch switch toward the unlocked position is configured to cause the shaft lock member to disengage from the handle lock member and thereby operatively uncouple the shaft assembly from the handle assembly in the released position.

Example 17

The surgical instrument of Example 16, wherein the latch system further comprises a cam base and the latch switch includes a cam lobe surface, wherein the cam lobe surface is configured to rotatably slide along the cam base to thereby urge the shaft assembly in a removal direction relative to the handle assembly from the released position toward a removal position for indicating the removal direction to a user.

Example 18

A method of removing a shaft assembly from a handle assembly of a surgical instrument, the surgical instrument having a latch system having a shaft lock member, a handle lock member, a cam base, and a latch member, the shaft lock member connected to the shaft assembly, the handle lock member connected to the handle assembly, wherein the handle lock member is configured to engage the shaft lock member and inhibit the shaft assembly from operatively uncoupling from the handle assembly, the latch member having a cam surface configured to engage the cam base, method comprising: (a) moving the latch member from a locked position toward a released position in order to disengage the shaft lock member from the handle lock member in the released position; (b) operatively uncoupling the shaft assembly from the handle assembly; (c) moving the latch member from the released position toward a removal position; and (d) engaging the cam surface of the shaft assembly against the cam base in order to urge the shaft assembly in a removal direction relative to the handle assembly for removal of the shaft assembly from the handle assembly.

Example 19

The method of Example 18, wherein the latch member comprises a latch button and moving the latch button further comprises sliding the latch button.

Example 20

The method of any one or more of Examples 18 through 19, wherein the latch member comprises a latch switch and moving the latch button further comprises pivoting the latch switch.

VII. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of removing a shaft assembly from a handle assembly of a surgical instrument, the surgical instrument having a latch system having a shaft lock member, a handle lock member, a cam base, and a latch member, the shaft lock member connected to the shaft assembly, the handle lock member connected to the handle assembly, wherein the handle lock member is configured to engage the shaft lock member and inhibit the shaft assembly from operatively uncoupling from the handle assembly, the latch member having a cam surface configured to engage the cam base, method comprising:
(a) moving the latch member from a locked position toward a released position in order to disengage the shaft lock member from the handle lock member in the released position;
(b) operatively uncoupling the shaft assembly from the handle assembly;
(c) moving the latch member from the released position toward a removal position; and
(d) engaging the cam surface of the shaft assembly against the cam base in order to urge the shaft assembly in a removal direction relative to the handle assembly for removal of the shaft assembly from the handle assembly.

2. The method of claim 1, wherein the latch member comprises a latch button and moving the latch button further comprises sliding the latch button.

3. The method of claim 1, wherein the latch member comprises a latch switch and moving the latch button further comprises pivoting the latch switch.

\* \* \* \* \*